(12) United States Patent
Akeno et al.

(10) Patent No.: US 6,487,759 B1
(45) Date of Patent: Dec. 3, 2002

(54) ENGAGING MEMBER AND MANUFACTURING METHOD THEREOF

(75) Inventors: Mitsuru Akeno, Toyama-ken (JP); Ryoichiro Uehara, Toyama-ken (JP); Shintaro Oosugi, Toyama-ken (JP)

(73) Assignee: YKK Corporation, Tokyo (JP)

( * ) Notice: Subject to any disclaimer, the term of this patent is extended or adjusted under 35 U.S.C. 154(b) by 0 days.

(21) Appl. No.: 09/712,232

(22) Filed: Nov. 15, 2000

(30) Foreign Application Priority Data

| Nov. 16, 1999 | (JP) | 11-325717 |
| Jan. 31, 2000 | (JP) | 2000-022350 |
| Aug. 1, 2000 | (JP) | 2000-232905 |

(51) Int. Cl.[7] .............................................. B65D 33/00
(52) U.S. Cl. ..................... 24/589.1; 24/399; 24/449; 24/629; 24/30.5 L; 24/698.1
(58) Field of Search ..................... 24/589.1, 399–405, 24/449, 698.1, 406, 408, 409, 625, 629, 621, 30.5 R, 30.5 L, 437

(56) References Cited

U.S. PATENT DOCUMENTS

| 3,173,184 A | * | 3/1965 | Ausnit | 24/399 |
| 4,874,186 A | * | 10/1989 | Groswith, III et al. | 24/67 P |
| 4,941,238 A | * | 7/1990 | Clark | 24/389 |
| 4,944,072 A | * | 7/1990 | Robson | 24/585.12 |
| 5,212,855 A | * | 5/1993 | McGanty | 24/452 |
| 5,794,315 A | * | 8/1998 | Crabtree et al. | 24/30.5 R |
| 6,009,603 A | * | 1/2000 | Gallagher | 24/399 |
| 6,058,577 A | * | 5/2000 | Ida et al. | 24/306 |
| 6,182,338 B1 | * | 2/2001 | Watanabe | 24/399 |
| 6,243,927 B1 | * | 6/2001 | Matsushima et al. | 24/401 |

* cited by examiner

Primary Examiner—J. J. Swann
Assistant Examiner—André L. Jackson
(74) Attorney, Agent, or Firm—Finnegan, Henderson, Farabow, Garrett & Dunner, L.L.P.

(57) ABSTRACT

The present invention provides an engaging member which enables a male member and a female member to be engaged with each other easily by sliding them relatively along the longitudinal direction and having a high engaging force, and a manufacturing method thereof. This engaging member includes the male member to be attached on one of components to be connected with each other and the female member to be attached on the other of the components. Engaging projecting portion with which the female member engages is provided on a side edge in the longitudinal direction of the male member. The female member includes an accommodating portion formed along the longitudinal direction so as to accommodate the male member. Hook-shaped portions with which the engaging projecting portion of the male member engages are formed along the longitudinal direction inside the accommodating portion. One of the accommodating portion of the male member and the female member has an engaging portion so as to protrude laterally and the other member includes an engaged portion with which the engaging portion engages.

9 Claims, 22 Drawing Sheets

ENGAGING MEMBER AND MANUFACTURING METHOD THEREOF

BACKGROUND OF THE INVENTION

1. Field of the Invention

The present invention relates to an engaging member for engaging end edge portions of separate components to be connected with each other and a manufacturing method thereof.

2. Description of the Related Art

Conventionally, there has been disclosed an air/water tightness mesh fastener which is an engaging member comprised of a male member and a female member such that they are flexible and can be engaged with each other due to elastic deformation, for example, in Japanese Utility Model Laid-Open Publication No. 5-76310. This fastener comprises a male engaging row and a female engaging row. The male engaging row is formed such that an entire section perpendicular to the longitudinal direction is in the shape of an arrow and engaging portions are provided on both sides of a head portion. The female engaging row is so formed that an entire section perpendicular to the longitudinal direction is shaped in letter U. Then, hooking portions are provided on opening edges of a U-shaped concave groove portion such that they oppose each other. Pressing portion is provided bridging side walls of the concave groove portion and a hollow portion is formed at a deeper position.

Engagement between the male engaging row and female engaging row is carried out by an engagement slider or manually. When a head portion of the male engaging row is inserted into the groove portion, the engaging portions engages with the hooking portions.

In case of the above described prior art, the male engaging row is pressed into the groove portion at right angle with respect to the longitudinal direction of the female engaging row so that the hooking portion is elastically deformed so as to achieve an engagement between the male engaging row and the female engaging row. Thus, an operation for adjusting the engagement position is troublesome and the engagement is not carried out easily if the members do not have some extent of stiffness in the engaging direction. Further, the female engaging row needs an appropriate elasticity because both engaging rows can be engaged with each other by respective elastic deformation, while the engaging force between the male engaging row and female engaging row increases as the stiffness of both increases. Therefore, easiness of engagement contradicts the engaging force. Further, the engaging member having this structure keeps the engagement against a force perpendicular to the longitudinal direction of the engaging portion. Therefore, this engaging member cannot resist a force parallel to the longitudinal direction. If an end portion in the longitudinal direction is not closed, the male engaging row is easily slipped out of the female engaging row.

SUMMARY OF THE INVENTION

The present invention has been achieved to solve the above described problems and therefore, an object of the invention is to provide an engaging member which enables a male member and a female member to be engaged with each other easily by sliding them relatively along the longitudinal direction and having a high engaging force and a manufacturing method thereof.

To achieve the above object, according to an aspect of the present invention, there is provided an engaging member comprising a male member to be attached on one of components to be connected with each other and a female member to be attached on the other of the components, engaging projecting portions with which the female member engages being provided on a side edge in the longitudinal direction of the male member, the female member including an accommodating portion formed along the longitudinal direction so as to accommodate the male member and hook-shaped portions with which the engaging projecting portion of the male member engages being formed along the longitudinal direction inside the accommodating portion. In the engaging member, one of the male member and the accommodating portion of the female member has an engaging portion so as to protrude and the other member includes an engaged portion with which the engaging portion engages.

Preferably, a plurality of the engaging portions are formed continuously along the engaging projecting portion of the male member and a plurality of the engaged portions are formed in the accommodating portion of the female member along the longitudinal direction. Further, the engaging portion has a face at right angle with respect to the longitudinal direction of the male member from a front end to a proximal end and a face inclined downward with respect to the longitudinal direction of the male member.

Further preferably, the aforementioned male member is engaged with the female member by inserting the engaging projecting portion from an end portion of the accommodating portion of the female member by sliding relatively in parallel. The shape of the engaging portion may be shaped in saw tooth wave, triangular wave, rectangular wave, trapezoidal wave or other.

According to another aspect of the present invention, there is provided an engaging member made of synthetic resin or the like, comprising a male member to be attached on one of components to be connected with each other and a female member to be attached on the other of the components, an engaging projecting portion with which the female member engages being provided on a side edge in the longitudinal direction of the male member, the female member including an accommodating portion formed along the longitudinal direction so as to accommodate the male member, and hook-shaped portions with which the engaging projecting portion of the male member engages being formed along the longitudinal direction inside the accommodating portion. In the engaging member, the male member has engaging pieces formed to extend at a predetermined pitch and elastically deformed within the accommodating portion of the female member and the female member contains at least an engaged portion with which the engaging pieces engage provided in the accommodating portion. The engaging pieces are extended inclinedly in an opposite direction with respect to the insertion direction into the female member and the engaged portion is composed of concave portion such as through hole formed within the accommodating portion.

Preferably, the engaging projecting portion of the male member is provided to protrude on both side faces along the longitudinal direction of the male member while the engaging pieces are formed continuously along a longitudinal edge of the male member. At least one of the end portions opposing each other when the male member and the female member engage with each other is cut out obliquely with respect to the insertion direction.

The aforementioned male member is engaged with the female member by inserting the engaging projecting portion from an end portion in the longitudinal direction of the accommodating portion of the female member by sliding relatively in parallel. The shape of the engaging portion may be shaped in wave, acute-angle triangular wave, narrow rectangular wave, narrow trapezoidal wave or other as long as it is flexible.

According to a still another aspect of the present invention, there is provided an engaging member made of synthetic resin or the like, comprising a male member to be attached on one of components to be connected with each other and a female member to be attached on the other of the components and formed to be flexible than the male member, engaging projecting portion with which the female member engages being provided on a side edge in the longitudinal direction of the male member, the female member including an accommodating portion formed so as to accommodate the male member and hook-shaped portions with which the engaging projecting portion of the male member engages being formed along the longitudinal direction inside the accommodating portion. In the engaging member, the male member has one or a plurality of engaging pieces formed so as to extend sideways thereof such that the male member is capable of sliding within the accommodating portion of the female member while deforming the female member and the female member contains one or a plurality of engaged portions with which the engaging pieces engage. The aforementioned engaged portion is formed of a concave portion such as a through hole formed within the accommodating portion.

The engaging piece has a face at right angle with respect to the longitudinal direction of the male member from its front end to its proximal end and a face inclined downward with respect to the longitudinal direction of the male member.

According to a further aspect of the present invention, there is provided a manufacturing method of an engaging member comprising the steps of: forming a male member to be attached on one of components to be connected with each other and a female member to be attached on the other of the components by extruding as a long member having a predetermined sectional shape; deforming side faces of the male member and female member as the long members by pressing with a pressing die heated at a predetermined temperature substantially at right angle with respect to the longitudinal direction thereof so as to form engaging portions and engaged portions engageable with each other: and cutting the long members into a predetermined length so as to form the respective engaging members.

According to another aspect of the invention, there is provided a manufacturing method of the engaging member, in which the male member to be attached on one of components to be connected with each other and the female member to be attached on the other of the components are formed by extrusion as a long member having a predetermined sectional shape. The male member and female member as the long members are punched out with a predetermined die or the like so as to form the engaging pieces and engaged portions. Then, the long members are cut into a predetermined length so as to form the respective engaging members.

The engaging member of the present invention achieves engagement of the male member and female member by sliding relatively in the longitudinal direction. With the connected state, the engaging projecting portion of the male member engages with the hook-shaped portion of the female member, thereby resisting a pulling force at right angle with respect to the longitudinal direction. Further, the engagement between the engaging pieces and engaged portions can resist a force in the longitudinal direction so that the connected state is maintained.

DESCRIPTION OF THE PREFERRED EMBODIMENTS

Figure 1:
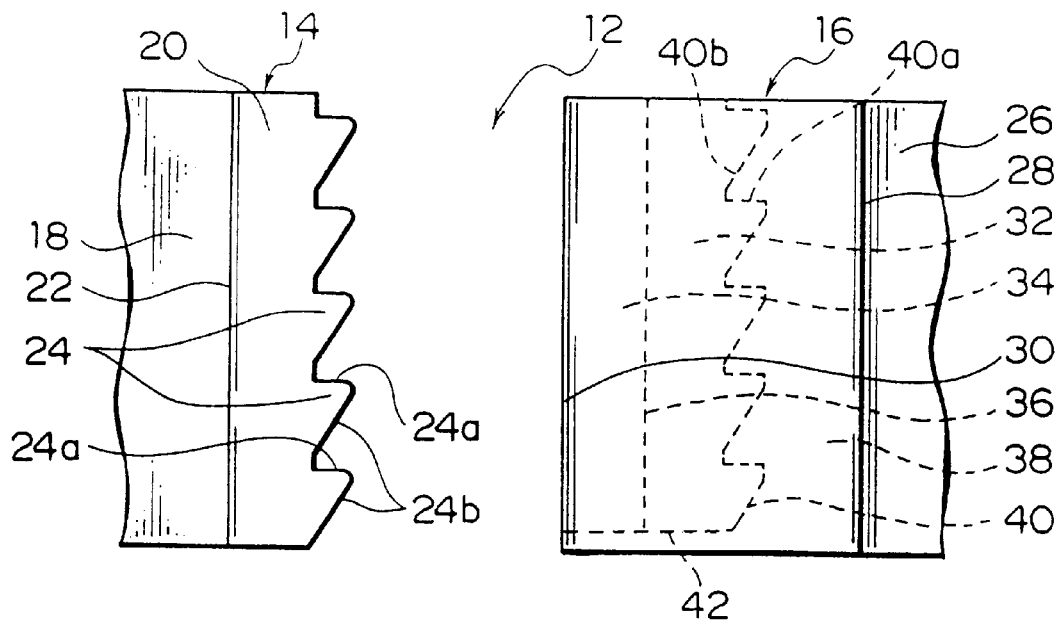
FIG. 1 is a front view of an engaging member according to a first embodiment of the present invention.

Hereinafter, the preferred embodiments of the present invention will be described in detail with reference to the accompanying drawings. FIGS. 1 to 7 show a first embodiment of the present invention. An engaging member 12 of this embodiment comprises a male member 14 and a female member 16, both made of synthetic resin having an appropriate elasticity such as nylon. The male member 14 is comprised of a flat base portion 18 and an engaging projecting portion 20 having an arrow-shaped section in a direction perpendicular to the longitudinal direction of the base portion 18 from a side edge along the longitudinal direction thereof. Side faces of the engaging projecting portion 20 on a side of the base portion 18 serves as engaging faces 22.

A plurality of engaging portions 24 each having a substantially saw-shaped section as viewed from front are provided continuously on an edge of the engaging projecting portion 20 along the longitudinal direction. An upper face 24a of the engaging portion 24 in FIG. 1 is a face at right angle to the longitudinal direction of the male member 14 while a lower face 24b is provided obliquely at a predetermined angle with respect to the longitudinal direction of the engaging projecting portion 20. This angle is about 20° to 40° with respect to the longitudinal direction, preferably about 30°.

The female member 16 is comprised of a long base portion 26 and a main body 28 protruded toward the male member 14 from the base portion 26, having a substantially U-shaped section. The main body 28 includes an groove-like opening 30 in which the base portion 18 of the male member 14 is fitted and movable and an accommodating portion 32 communicating with the opening 30, both provided along the longitudinal direction. The opening 30 and accommodating portion 32 are open at a top end in the longitudinal direction of the main body 28 and a bottom end thereof is fused by heat.

A hook shaped portion 34 having a triangular section is formed on an inner face of the side edge of the opening 30 such that it is protruded toward a center line along the longitudinal direction of the accommodating portion 32. An inner face of the hook shaped portion 34 on the side of the accommodating portion 32 acts as an engaged face 36 which comes into contact with an engaging face 22 of the engaging projecting portion 20 of the male member 14.

A rise-up portion 38 protruded toward the opening 30 is formed along the longitudinal direction on a bottom of the accommodating portion 32. A plurality of saw-shaped engaged portions 40 with which the engaging portion 24 of the male member 14 engages are provided continuously along an end of the rise-up portion 38. A lower face 40a of the engaged portion 40 in FIG. 1 is parallel to the protruding direction of the rise-up portion 38 while an upper face 40b is formed obliquely at a predetermined angle with respect to the protruding direction of the rise-up portion 38. The engaged portion 40 is formed in the same shape such that it has concave and convex portions complementarily in a reverse direction to the engaging portion 24.

Figure 4:
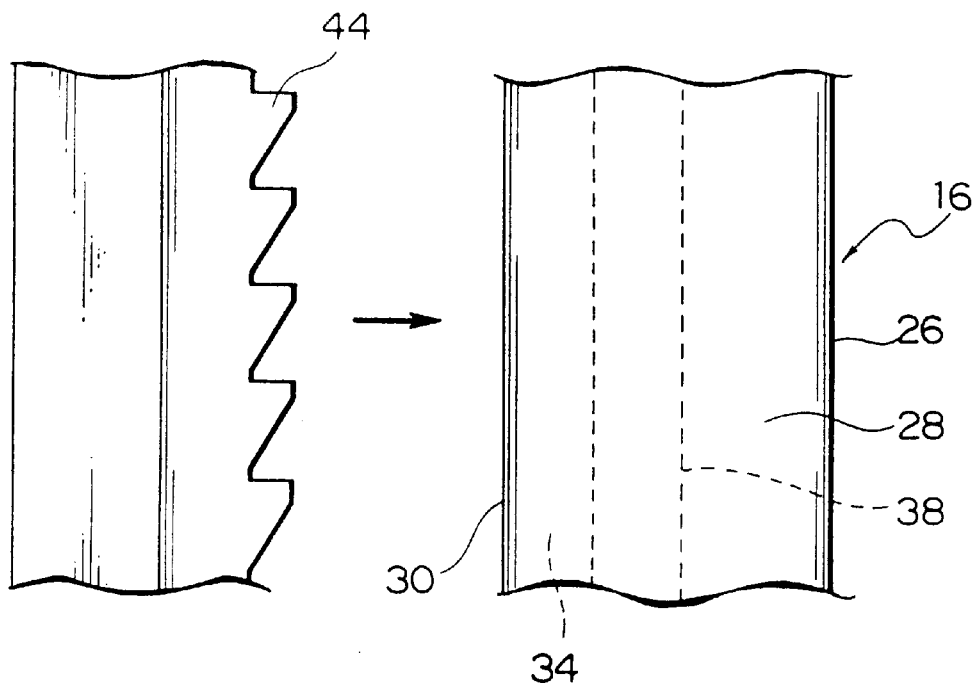
FIG. 4 is a front view showing a manufacturing method of the engaging member according to this embodiment.
Figure 5:
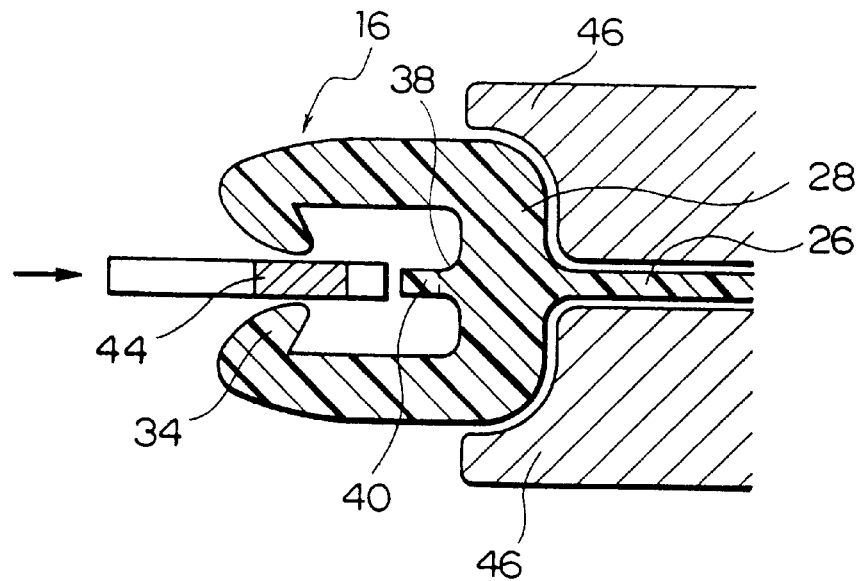
FIG. 5 is a cross sectional view showing a manufacturing method of the engaging member according to this embodiment.

Next, a manufacturing method of the engaging member 12 of this embodiment will be described. First, the female member 16 is formed as a long member comprised of the base portion 26 and main body 28 by continuous extrusion. Next, as shown in FIGS. 4 and 5, a pressing die 44 formed in a negative shape to the engaged portion 40, having continuous saw-shaped teeth is heated at a predetermined temperature and pressed against an end of the rise-up portion 38 of the main body 28. At this time, the female member 16 is fixed on a jig 46. Consequently, the end portion of the rise-up portion 38 of the main body 28 is melted and deformed by heat so as to form the engaged portion 40. This action is repeated several times while shifting a position thereof at a pitch corresponding to the length of the pressing die 44, so that the engaged portion 40 is formed continuously in the long member of the female member 16. After that, the long member of the female member 16 is cut into a predetermined length depending on the application and the bottom end is fused by heat so as to form a fused portion 42. As a result, individual female members 16 are completed. Further, the male member 14 is also formed continuously as a long member comprised of the base portion 18 and engaging projecting portion 20 by extrusion. After that, the engaging portion 24 is formed on an edge of the engaging projecting portion 20 of this long member by a pressing die (not shown) having a predetermined thickness.

Figure 6:
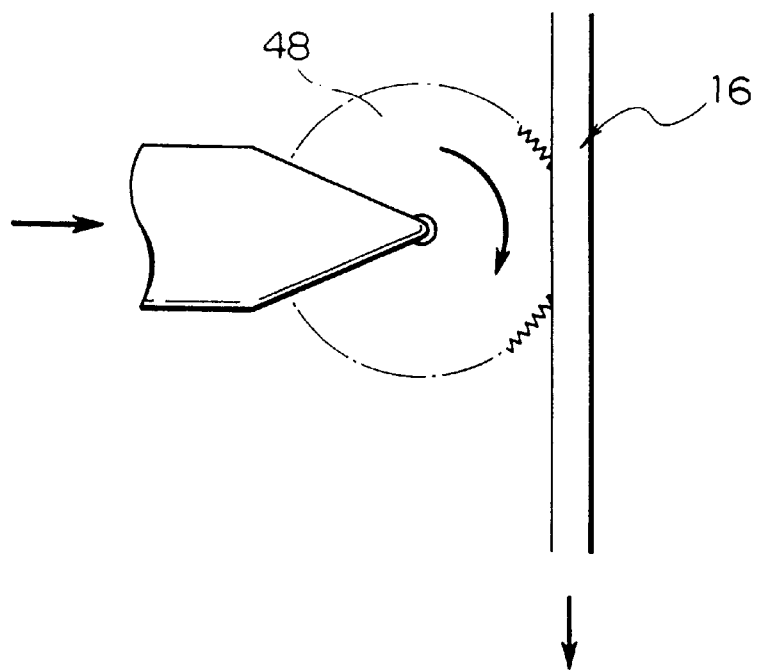
FIG. 6 is a front view showing another manufacturing method of the engaging member according to this embodiment.

As another manufacturing method, the engaged portion 40 of the female member 16 or the engaging portion 24 of the male member 14 may be formed continuously by means of a circular pressing die 48 having the same teeth as the pressing die 44 provided around the periphery thereof as shown in FIG. 6.

Figure 2:
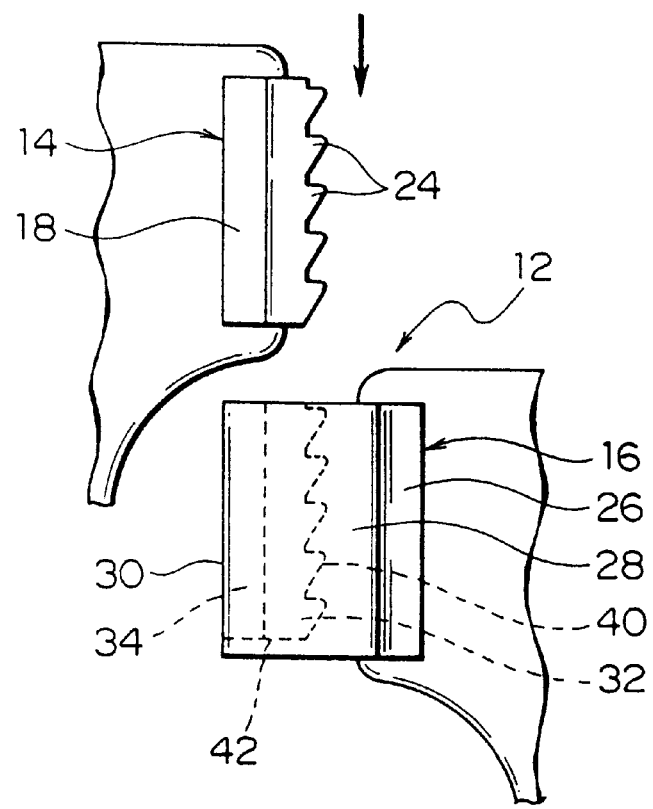
FIG. 2 is a front view showing an engaging operation for the engaging member according to this embodiment.

Next, a method for use of the engaging member 12 of this embodiment will be described. When it is intended to engage the male member 14 with the female member 16 of the engaging member 12, as shown in FIG. 2, the male member 14 is brought into the female member 16 through an upper end in FIG. 1, such that the engaging projecting portion 20 of the male member 14 is inserted into the accommodating portion 32 of the female member 16. At this time, the base portion 18 of the male member 14 is located within the opening 30 of the female member 16. Upon the insertion, the engaging portion 24 of the male member 14 is fitted to the engaged portion 40 of the female member 16. However, if the male member 14 is pressed into the female member 16 by applying more than a predetermined force, the engaging portion 24 and the engaged portion 40 are elastically deformed or the main body 28 of the female member 16 is slightly deformed elastically. Thus, the engaging portion 24 can move over the engaged portion 40. Further, because the face 24b of the engaging portion 24 of the male member 14 and the face 40b of the engaged portion 40 of the female member 16, which come into contact with each other when the male member 14 is inserted, are both inclined with respect to the insertion direction of the male member 14, the engaging portion 24 can go over the engaged portion 40 easily if some extent of force is applied. As a result, the male member 14 can slide within the accommodating portion 32 of the female member 16. Then, the bottom end of the male member 14 comes into contact with the fused portion 42 at the bottom of the female member 16 and is stopped.

Figure 3:
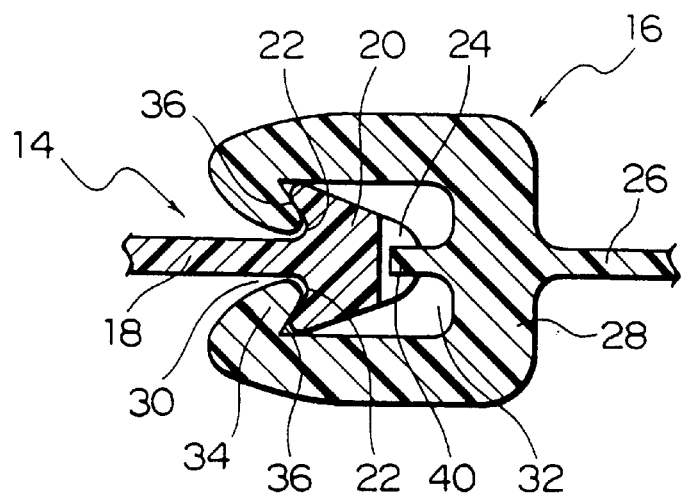
FIG. 3 is a cross sectional view showing an engagement state of the engaging member of this embodiment.

With this state, the engaging portion 24 of the male member 14 engages with the engaged portion 40 of the female member 16 as shown in FIG. 3, so that the face 24a opposes the face 40a in a contact state, thereby preventing the male member 14 from being slipped out in a direction opposite to the insertion direction. When a force is applied to the male member 14 and the female member 16 in such a direction perpendicular to the length thereof that they depart from each other, the engaging faces 22 of the engaging projecting portion 20 of the male member 14 come into contact with the engaged faces 36 of the hook shaped portion 34 of the female member 16, thereby preventing the male member 14 from being escaped from the opening 30 of the female member 16.

When it is intended to release the engagement of the engaging member 12, conversely, the male member 14 is pulled upward as viewed in the Figure with respect to the female member 16. Although the face 24a of the engaging portion 24 of the male member 14 and the face 40a of the engaged portion 40 of the female member 16 are located substantially at right angle with respect to the pulling-up direction of the male member 14 so that they oppose each other, a large resistance is generated. However, if the male member 14 is pulled up at a stronger force than a predetermined level, the respective members are elastically deformed, so that the male member 14 can be pulled out of the female member 16 thereby releasing the engagement therebetween. Alternatively, it is permissible to so construct that the engagement can be never released by suppressing the elastic deformation of the female member 16 and the like so as to intensify the engagement between the engaging portion 24 and the engaged portion 40.

Figure 7:
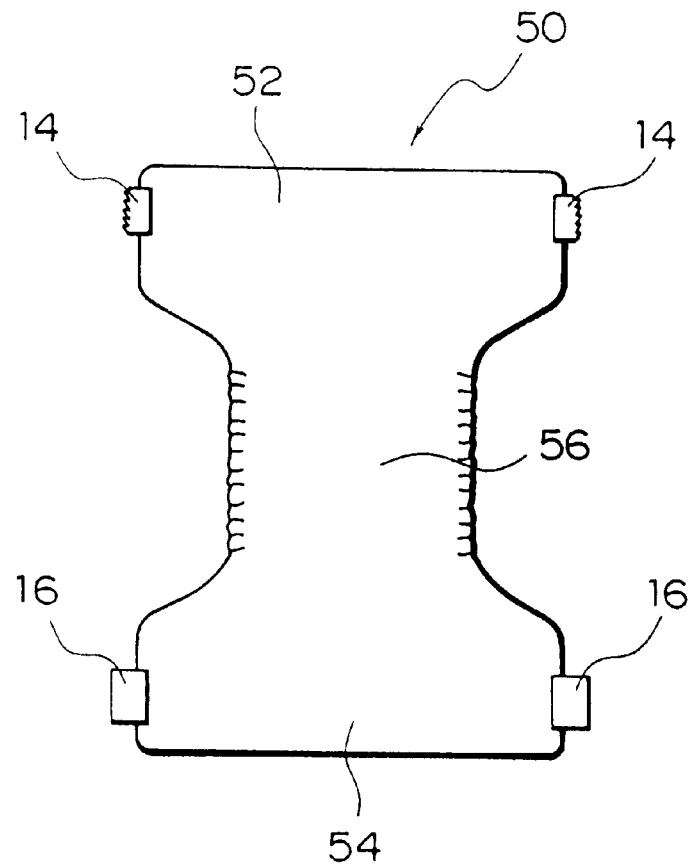
FIG. 7 is a front view showing an example of use of the engaging member according to this embodiment.

Next, an example of use of the engaging member 12 of this embodiment is shown. As shown in FIG. 7, the engaging member 12 can be applied to a disposable diaper 50. The disposable diaper 50 is comprised of a buttock portion 52 for wrapping the buttocks, an abdomen portion 54 for wrapping the abdomen and a crotch portion 56 located between the buttock portion 52 and the abdomen portion 54 such that they are integrated. The male member 14 of the engaging member 12 is attached to each side portions of the buttock portion 52. The female member 16 of the engaging member 12 is attached to each side portions of the abdomen portion 54. Then, with the disposable diaper 50 put on a baby's body as a wearer, the side portions of the buttock portion 52 and the abdomen portion 54 are matched with each other near the sides of his abdomen, and the male members 14 are inserted into the female members 16 so that they are engaged with each other.

According to the engaging member 12 of this embodiment, the male member 14 can be easily connected with the female member 16 by sliding the former along the longitudinal direction of the latter. Even when a force is applied in any direction, for example, in a direction that the male member 14 departs from the female member 16 at right angle relative to the length thereof or in a direction that the male member 14 is pulled out upwardly, the engagement between the male member 14 and the female member 16 is hardly released thereby securing the safety. Particularly when the disposable diaper 50 or the like is made of flexible material, the pressing operation is difficult to carry out because the material has no stiffness. However, according to the engaging member 12 of this embodiment, the male and female members only have to be slid relative to each other along the longitudinal direction at the time of insertion, thereby not necessitating the pressing operation or the like. Thus, the inserting operation can be carried out easily. Further, when this engaging member is applied to the disposable diaper 50, there is no possibility that the baby's abdomen may be pushed, so that no discomfort is given to him or her. Further, because the engagement is carried out by insertion, the opening 30 in the main body 28 of the female member 16 does not have to be opened widely upon the engagement and therefore, this engaging member can be made of hard material. Thus, this engaging member can have a strong connecting force.

Figure 12:
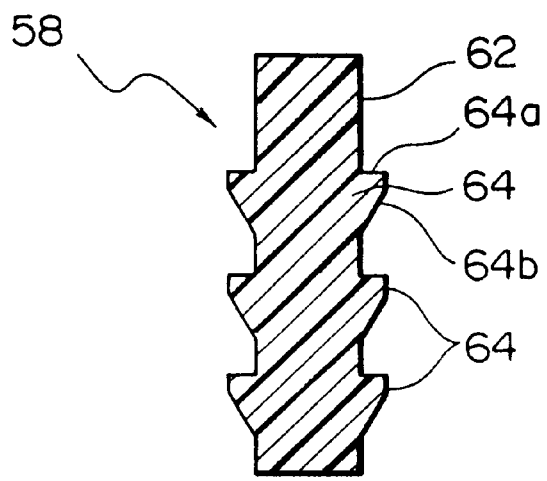
FIG. 12 is a longitudinal sectional view taken along the line XII—XII of FIG. 11.
Figure 13:
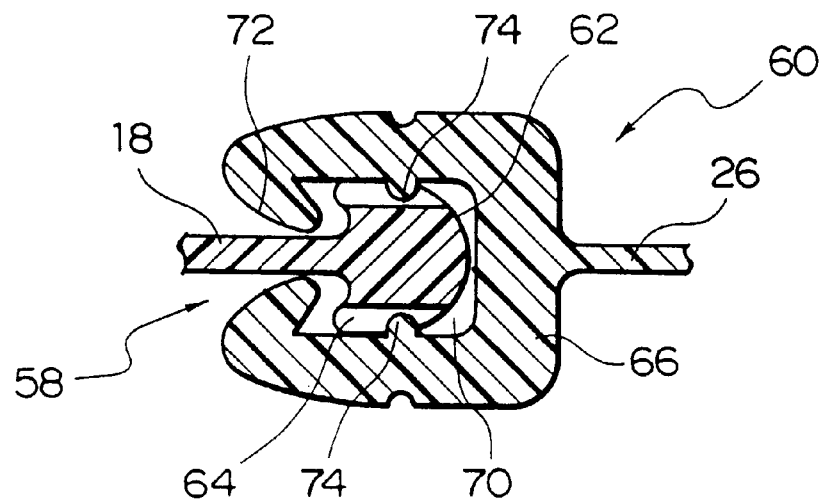
FIG. 13 is a cross sectional view showing an engagement state. of the engaging member according to this embodiment.
Figure 14:
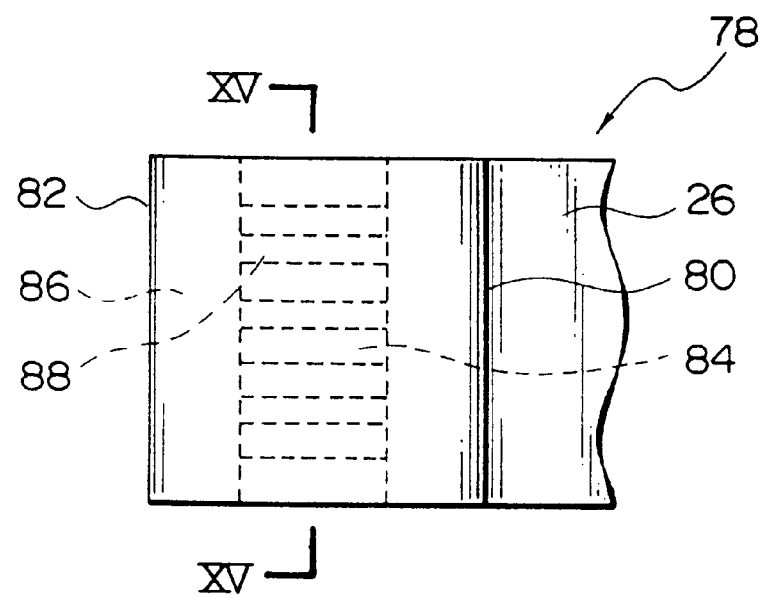
FIG. 14 is a front view of the female member of the engaging member according to a third embodiment of the present invention.
Figure 15:
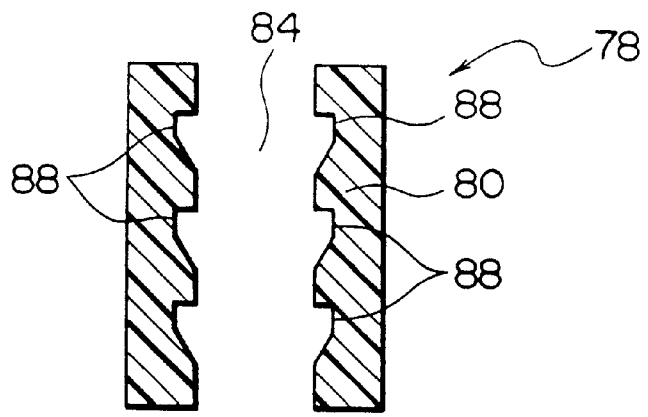
FIG. 15 is a longitudinal sectional view taken along the line XV—XV of FIG. 14.

Next, a second embodiment of the present invention will be described with reference to FIGS. 8 to 13. Here, the same reference numerals are attached to the same components as the above described embodiment and a description thereof is omitted. The engaging member of this embodiment is also comprised of a male member 58 and a female member 60. The male member 58 is comprised of a long base portion 18 and an engaging projecting portion 62 which is protruded from the base portion 18 and located at a side toward the female member 60. The engaging projecting portion 62 is formed in the shape of an arrow in cross-section such that both side portions in a direction perpendicular to the protruding direction of the engaging projecting portion 62 are thick. On both side faces of the engaging projecting portion 62 in the longitudinal direction, three engaging portions 64 are arranged in parallel in the longitudinal direction. In FIG. 12, an upper face 64a of the engaging portion 64 is located at right angle with respect to the longitudinal direction of the base portion 18 and a lower face 64b is provided obliquely at a predetermined angle with respect to the longitudinal direction, for example, 20° to 40°, preferably 30°.

Figure 8:
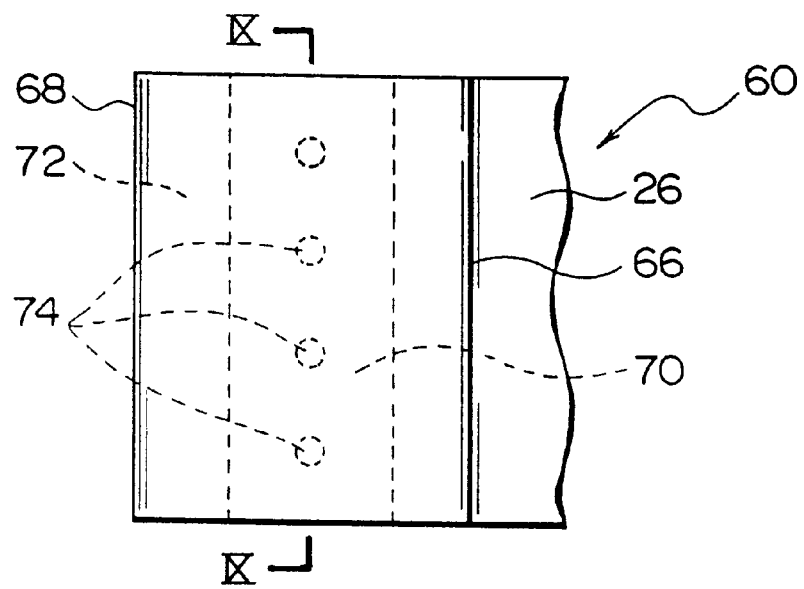
FIG. 8 is a front view showing a female member of the engaging member according to a second embodiment of the present invention.
Figure 9:
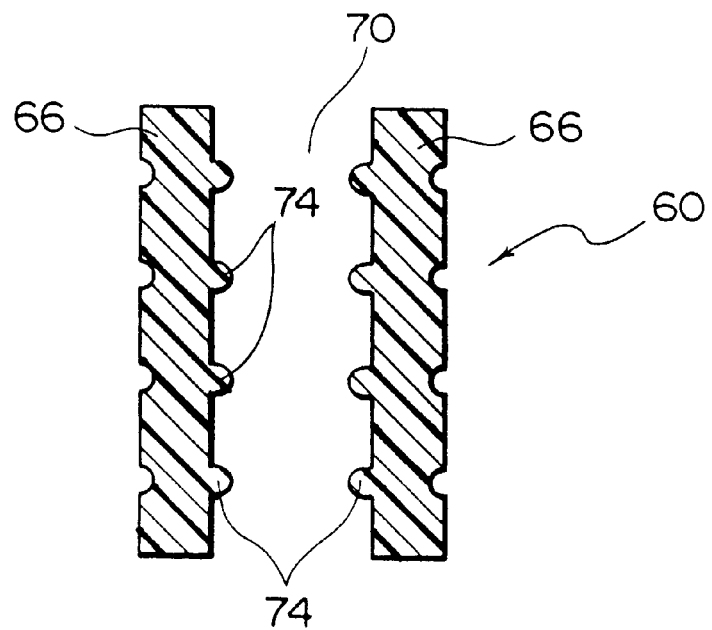
FIG. 9 is a longitudinal sectional view taken along the line IX—IX of FIG. 8.

As shown in FIG. 8, the female member 60 is comprised of a long base portion 26 and a U-shaped main body 66 protruded toward the male member 58 from the base portion 26. The main body 66 includes a groove-like opening 68 in which the base portion 18 of the male member 58 is capable of moving and an accommodating portion 70 communicating with the opening 68. A hook-shaped portion 72 is formed on an inner face of a side edge of the opening 68 such that it is protruded toward the center of the accommodating portion 70. Four protrusions 74, which are engaged portions, are arranged in row in the longitudinal direction on an inner face of each of both sides of the main body 66 opposing each other.

Figure 10:
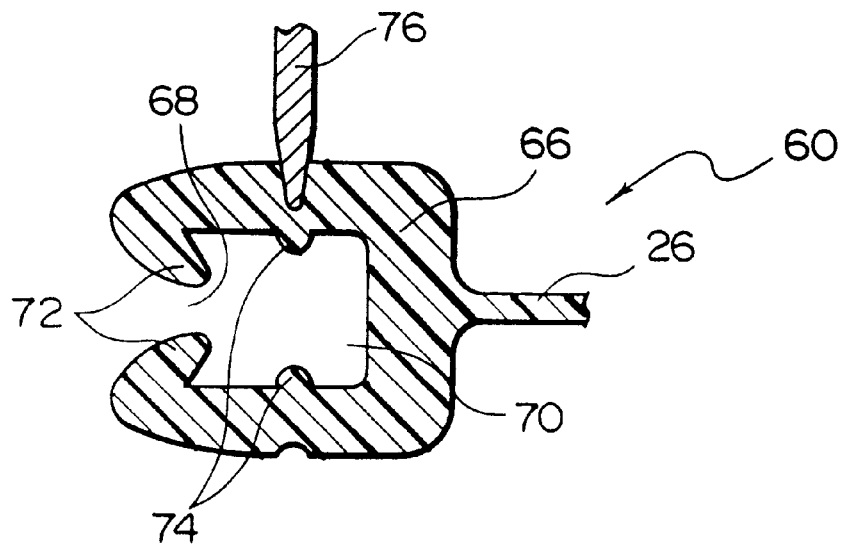
FIG. 10 is a cross sectional view showing a manufacturing method of the female member of the engaging member according to this embodiment.
Figure 11:
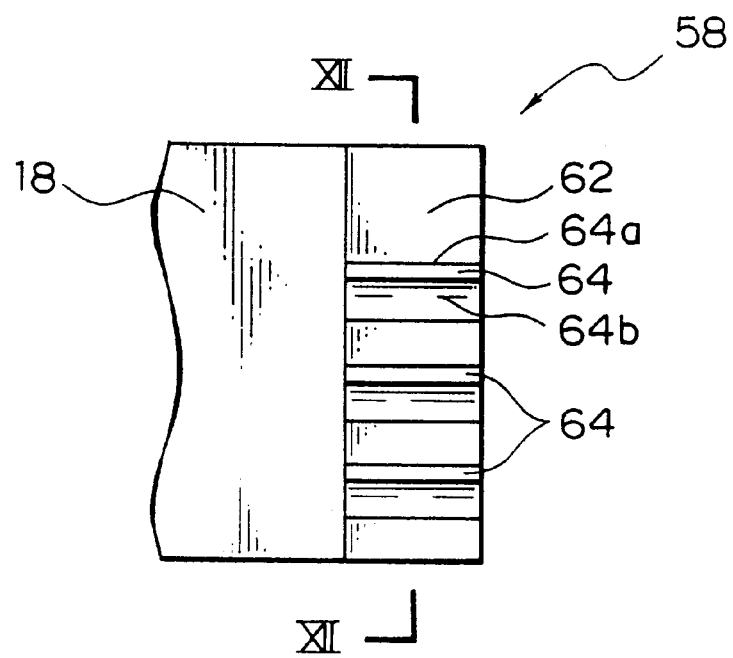
FIG. 11 is a front view showing a male member of the engaging member according to this embodiment.

Next, a manufacturing method of the female member 60 of the engaging member of this embodiment will be described with reference to FIG. 10. First, a long member comprised of the base portion 26 and the main body 66 is formed continuously by extrusion as the female member 60. Then, a bar-like pressing die 76 having substantially the same diameter as the protrusion 74 is heated at a predetermined temperature and pressed at a predetermined position from outside of each of both sides of the main body 66 toward inside of the main body 66. Consequently, the main body 66 is deformed by heat so that some portion is protruded into the accommodating portion 70 by the pressing die 76 so as to form the protrusion 74. Like the first embodiment, the male member 58 is formed by pressing both side faces of the engaging projecting portion 62 by a heated pressing die.

Next, a method of use of the engaging member of this embodiment will be described. When it is intended to engage the male member 58 with the female member 60, the male member 58 is inserted into the female member 60 through an end portion of the accommodating portion 70, located up in FIG. 8 and moved downward. Although the engaging portion 64 of the male member 58 comes into contact with the protrusion 74 of the female member 60 so that a resistance is generated, the respective members are elastically deformed, so that the protrusion 74 goes over the oblique face 64b of the engaging portion 64. Then, if some extent of force is applied, the male member 58 can be slid easily. When the engagement is maintained, the face 64a of the engaging portion 64 of the male member 58 engages with the protrusion 74 of the female member 60, so that the male member 58 is never slipped out easily. If it is intended to release the engagement, by pulling up the male member 58 at a force stronger than a predetermined level, the male member 58 can be pulled out of the female member 60, thereby the engagement being released.

The engaging member of this embodiment exerts the same effect as the above described embodiment. Particularly because the engaging portions 64 are formed on both sides of the engaging projecting portion 62, a high engaging force is ensured.

Next, a third embodiment of the present invention will be described with reference to FIGS. 14 to 19. For the engaging member of this embodiment, the same reference numerals are attached to the same components as the above described embodiment and a description thereof is omitted. A female member 78 of this embodiment is comprised of a base portion 26 and a main body 80 protruded from the base portion 26 toward the male member 58, having a substantially U-shaped section. The main body 80 is comprised of a groove-like opening 82 in which the base portion 18 of the male member 58 is movable and an accommodating portion 84 communicating with the opening 82. Hook-shaped portions 86 are formed on inner faces of the side edges on the opening 82 such that they are projected toward the center of the accommodating portion 84. Four engaged portions 88 are arranged in row on inner faces on both sides of the main body 80, in the up/down direction of the same Figure.

Figure 16:
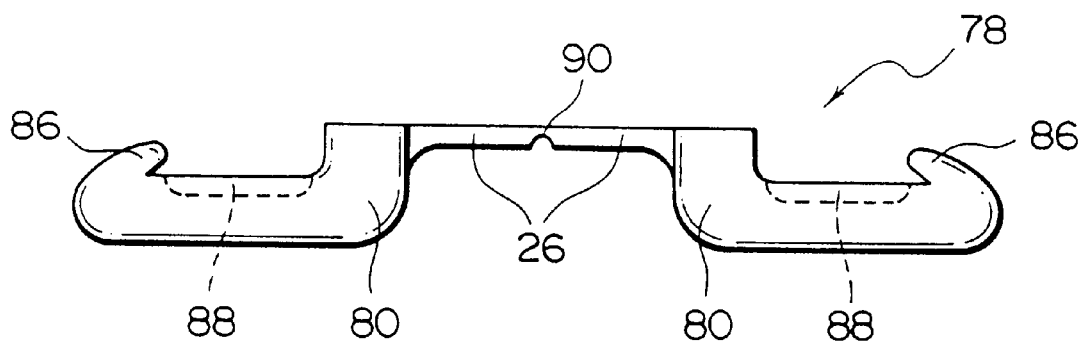
FIG. 16 is a plan view showing a manufacturing method of the female member of the engaging member according to this embodiment.
Figure 17:
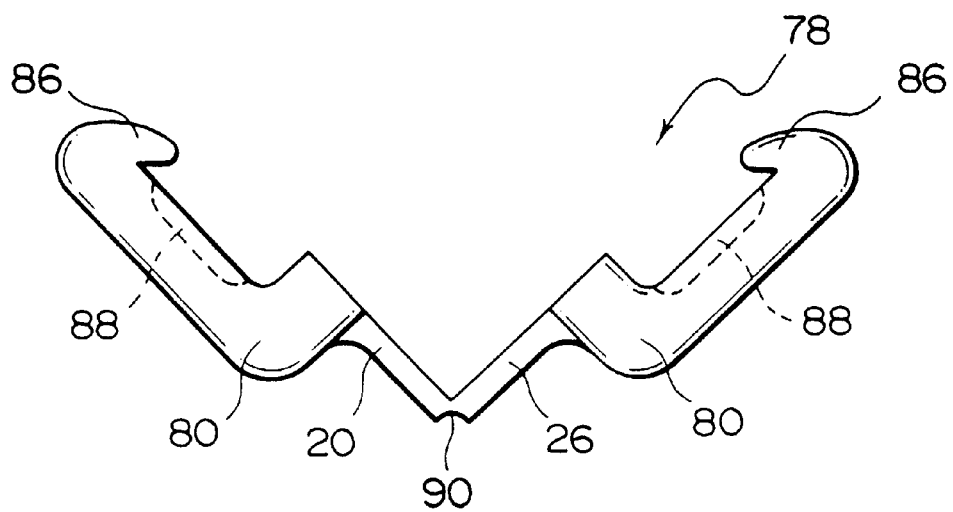
FIG. 17 is a plan view showing the manufacturing method of the female member of the engaging member according to this embodiment.
Figure 18:
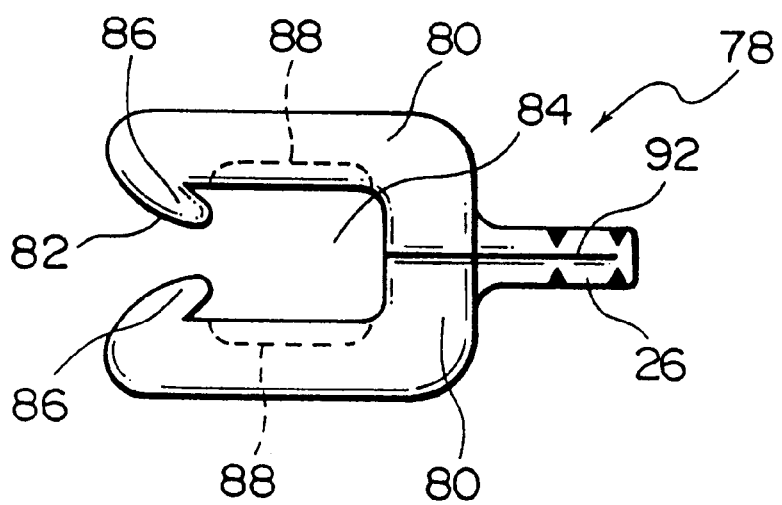
FIG. 18 is a plan view showing the manufacturing method of the female member of the engaging member according to this embodiment.

A manufacturing method of the female member 78 of the engaging member of this embodiment will be described with reference to FIGS. 16 to 18. The female member 78 is formed in a state that the base portion 26 and the main body 80 are divided to two sections in a direction parallel to both sides of the base portion 26. Upon molding, the female member 78 is formed by extruding a long member continuously. A thin hinge portion 90 is formed integrally between a pair of the divided base portions 26. Then, engaged portions 88 are formed in inner faces of the main body 80 as shown in FIG. 16 by the same manufacturing method as the first embodiment. As shown in FIGS. 17 and 18, the female member 78 is folded at the hinge portion 90 and fused in the thickness direction of the base portion 26 from outside so as to form a heat press-fitting portion 92. As a result, the female member 78 is completed.

Figure 19:
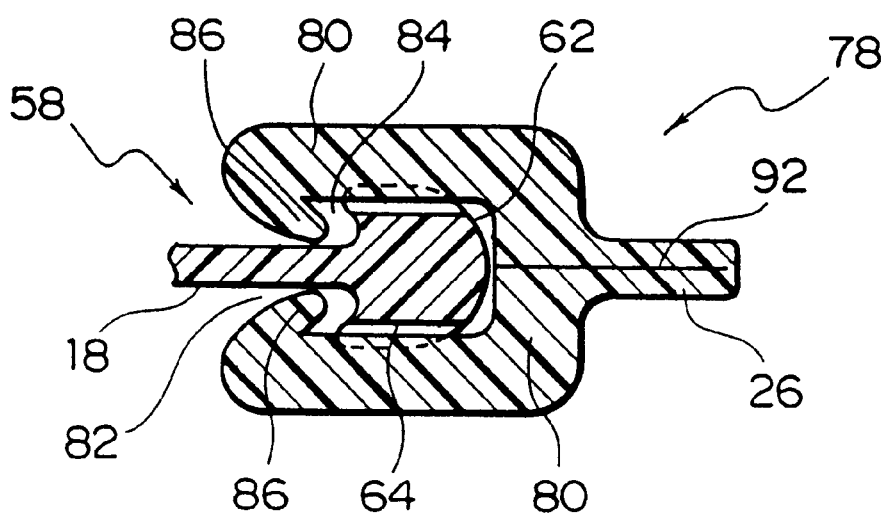
FIG. 19 is a cross sectional view showing an engagement state of the engaging member according to this embodiment.
Figure 20:
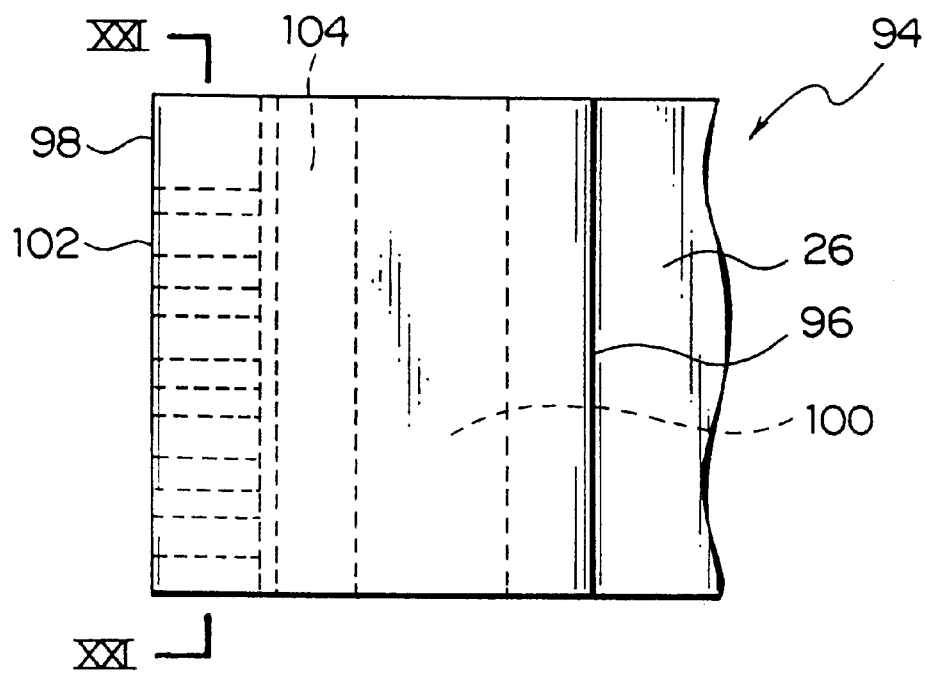
FIG. 20 is a front view of the female member of the engaging member according to a fourth embodiment of the present invention.
Figure 21:
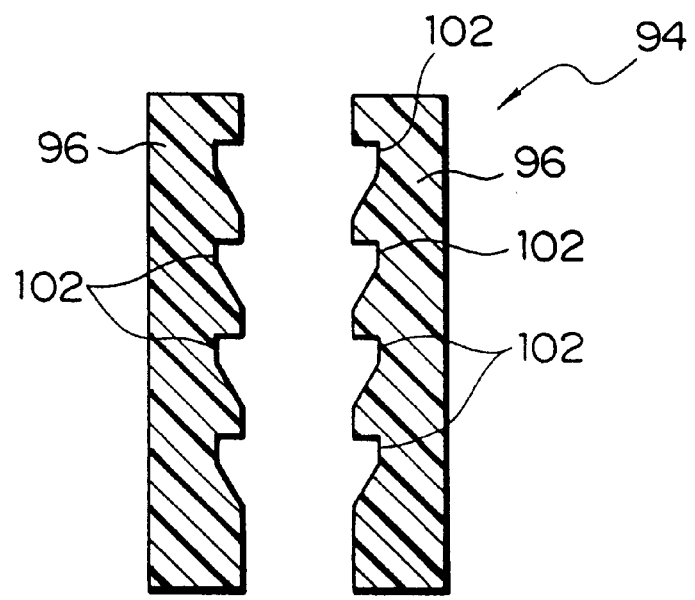
FIG. 21 is a longitudinal sectional view taken along the line XXI—XXI of FIG. 20.
Figure 22:
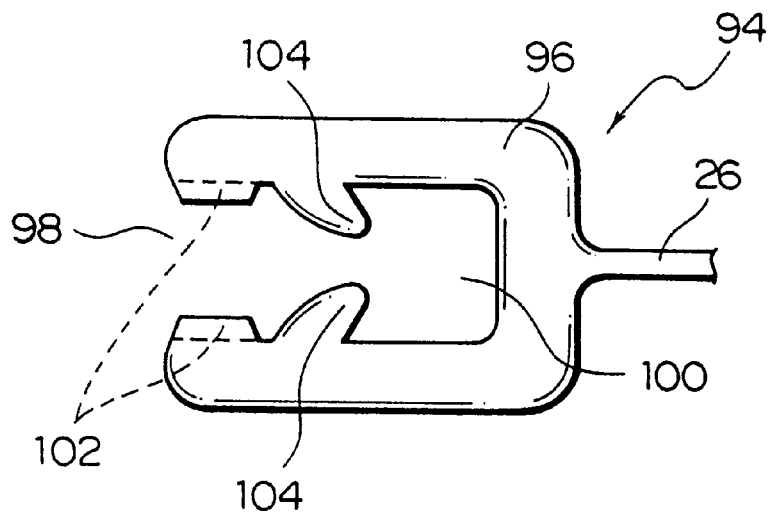
FIG. 22 is a plan view of the female member of the engaging member according to this embodiment.
Figure 23:
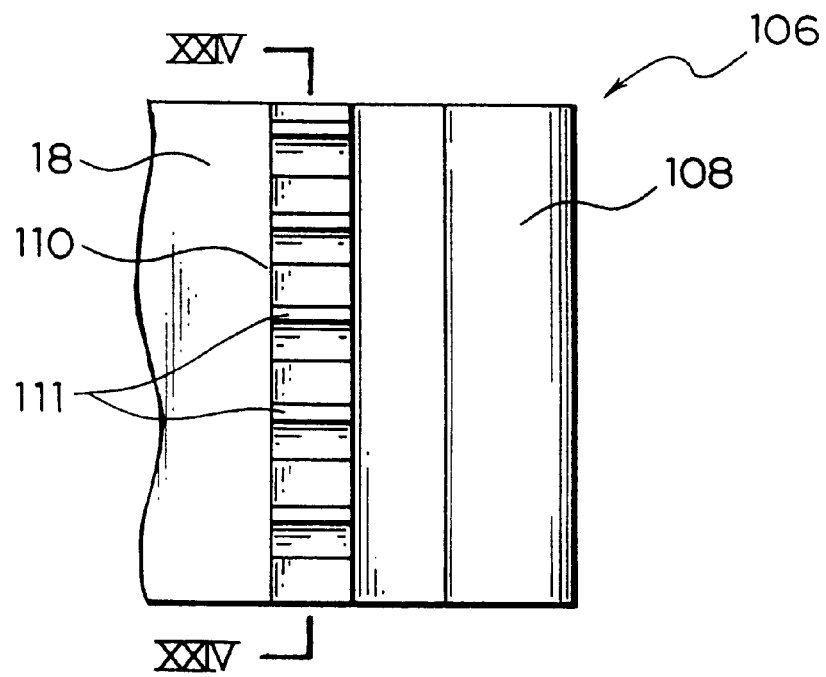
FIG. 23 is a front view of the male member of the engaging member according to this embodiment.
Figure 24:
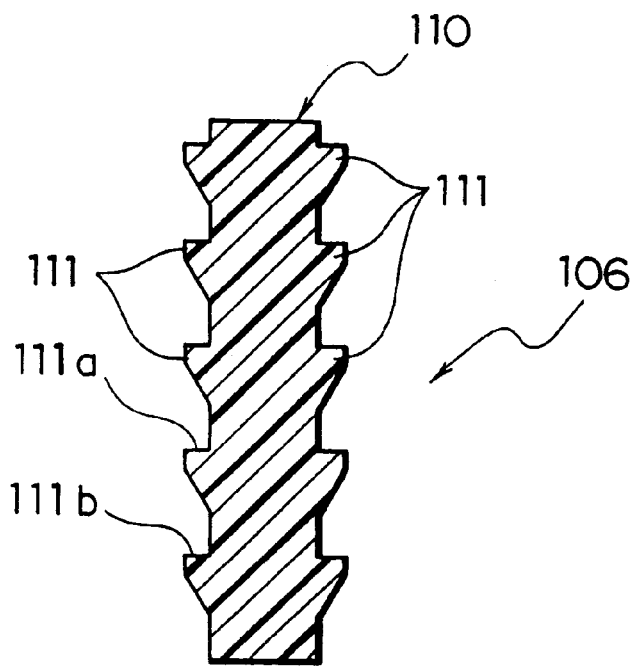
FIG. 24 is a longitudinal sectional view taken along the line XXIV—XXIV of FIG. 23.
Figure 25:
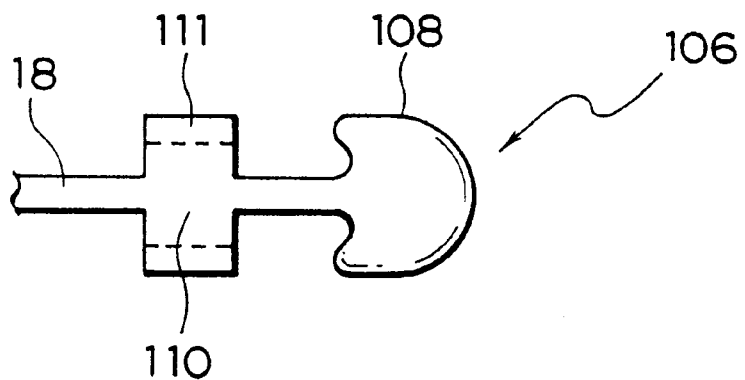
FIG. 25 is a plan view of the male member of the engaging member according to this embodiment.

The method of use of the engaging member of this embodiment is the same as the above described respective embodiments. For example, this female member engages with the male member 58 of the second embodiment. Consequently, as shown in FIG. 19, the engaging portion 64 of the male member 58 engages with the engaged portion 88 of the female member 78, thereby securing a strong engaging force like the above respective embodiments. Further, according to the manufacturing method of the engaging member of this embodiment, the engaged portions 88 can be formed easily on inner faces of both sides of the main body 80.

Next, a fourth embodiment of the present invention will be described with reference to FIGS. 20 to 26. For the engaging members of this embodiment, the same reference numerals are attached to the same components as the above described embodiments and a description thereof is omitted. A female member 94 of this embodiment is comprised of a base portion 26 and a main body 96 having a substantially U-shaped section which is protruded from the base portion 26 toward a male member 106, which will be described later. The main body 96 includes a groove-like opening 98 in which the base portion 18 of the male member 106 is movable and an accommodating portion 100 communicating with the opening 98. Four engaged portions 102 are arranged in row in the longitudinal direction on an inner face of each of both sides adjacent a side edge of the opening 98. Then, hook-shaped portions 104 are formed in the longitudinal direction on inner faces nearer to the bottom of the accommodating portion 100 comparing to the engaged portions 102, such that they are protruded toward the center of the accommodating portion 100.

The male member 106 of this embodiment is comprised of a base portion 18 and an engaging projecting portion 108, which is protruded from the base portion 18 toward the female member 94. The engaging projecting portion 108 is formed in the shape of an arrow such that it is thicker at right angle with respect to the protruding direction of the engaging projecting portion 108. A step portion 110, which is thick at right angle with respect to the protruding direction of the engaging projecting portion 108, is formed between a proximal end of the engaging projecting portion 108 and the base portion 18. Five engaging portions 111 are arranged in row in the longitudinal direction on the surface of the step portion 110. The engaging portion 111 includes a face 111a at right angle to the longitudinal direction of the male member 106 and a face 111b inclined downward with respect to the longitudinal direction of the male member 106.

Figure 26:
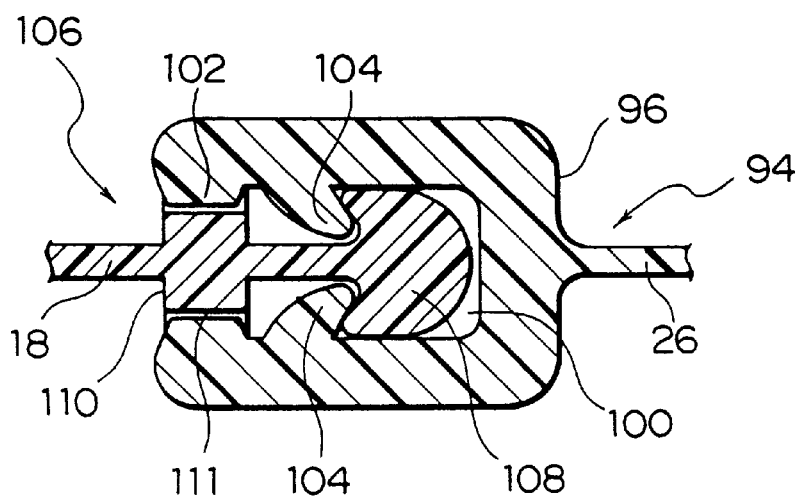
FIG. 26 is a cross sectional view showing an engagement state of the engaging member according to this embodiment.

The manufacturing method of the engaging member of this embodiment is the same as the third embodiment and further, the method of use thereof is the same. As shown in FIG. 26, the engaging portion 111 of the male member 106 engages with the engaged portion 102 of the female member 94 so as to prevent the male member 106 from being moved in parallel to the insertion direction. Further, an engaging projecting portion 108 engages with the hook-shaped member 104 of the female member so as to prevent the male member 106 from being slipped out at right angle with respect to the insertion direction of the male member 106. Because the independent engagement of engaging members are provided in two directions, a strong engaging force can be secured, so that the male member can engage with the female member firmly.

Next, a fifth embodiment of the present invention will be described with reference to FIGS. 27 to 34. FIGS. 27 to 34 show an engaging member 112 of this embodiment, which is comprised of a male member 114 and a female member 116 each made of olefin base resin having an appropriate elasticity such as polypropylene, polyethylene or the like or other synthetic resin such as semi-rigid vinyl chloride. The male member 114 is comprised of a flat base portion 118 and engaging projecting portion 120 formed on both sides of a side edge along the longitudinal direction of the base portion 118 in parallel to the longitudinal direction. Then, a side face on the side of the base portion 118 of each engaging projecting portion 120 is formed as an engaging face 122 to engage with the female member 116. Further, wave-like engaging pieces 124 are formed at a predetermined pitch along the longitudinal direction on a front edge between the respective engaging projecting portions 120. The engaging piece 124 may be formed in any shape as long as it is capable of being elastically distorted in an opposite direction to the insertion direction into the female member 116. This engaging piece 124 may be of narrow triangle with a sharp vertex or narrow trapezoid as well as wave shape. A bulged portion 128, which is slightly bulged from the base portion 118 of the male member 114, is formed on both side faces of the base portion 118 on an opposite side to the engaging piece 124 such that it is located apart at a predetermined interval from and in parallel to the engaging projecting portion 120. This bulged portion 128 guides a hook-shaped portion 134 of the female member, which will be described later.

The female member 116 is comprised of a pair of parallel front and rear wall portions 133 and a side wall portion 135 connecting ends of the front and rear wall portions 133, and formed to have a substantially U-shaped section with an opening 126 at one side edge which engages with the male member 114. The base portion 118 of the male member 114 is formed so as to be capable of moving in that opening 126. Further, the female member 116 includes an accommodating portion 132 communicating with the opening 126, provided in the longitudinal direction. A hook-shaped portion 134 having a substantially triangular section, which is protruded toward the center line of the accommodating portion 132 along the longitudinal direction, is formed along the longitudinal direction inside of each of the side edge portions opposing at the opening 126. A front end on the side of the accommodating portion 132 of the hook-shaped portion 134 acts as an engaged face 136 which comes into contact with the engaging face 122 of the engaging projecting portion 120 of the male member 114. Through holes 138, which are engaged portions, are formed at a predetermined pitch in the longitudinal direction on the side wall portion 135 of the accommodating portion 132. A plurality of the through holes 138 are provided so that the front ends of the engaging pieces 124 of the male member 114 engage therewith. Meanwhile, the engaged portions may be convex portions or concave portions as well as the through holes 138 and may be one.

Figure 30:
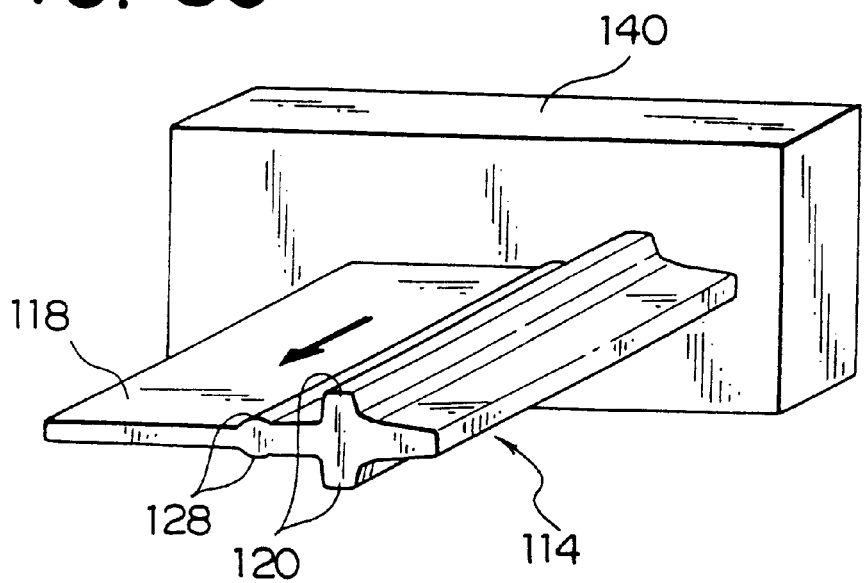
FIG. 30 is a perspective view showing a manufacturing method of the male member of the engaging member according to this embodiment.
Figure 31:
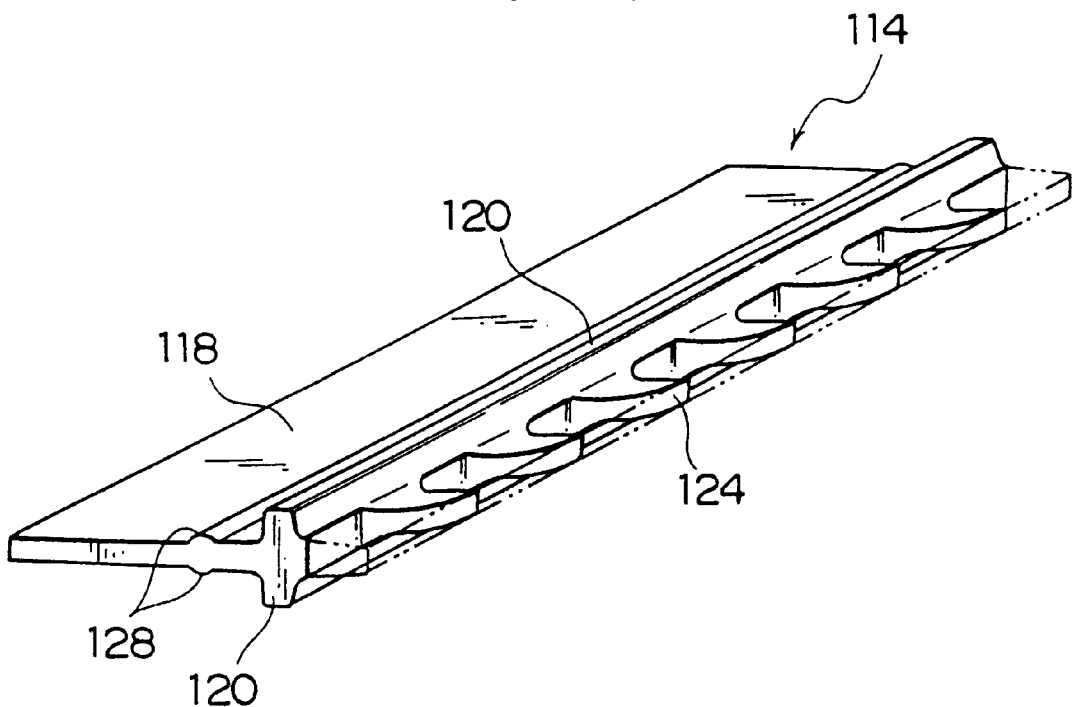
FIG. 31 is a perspective view showing the male member of the engaging member according to this embodiment.
Figure 32:
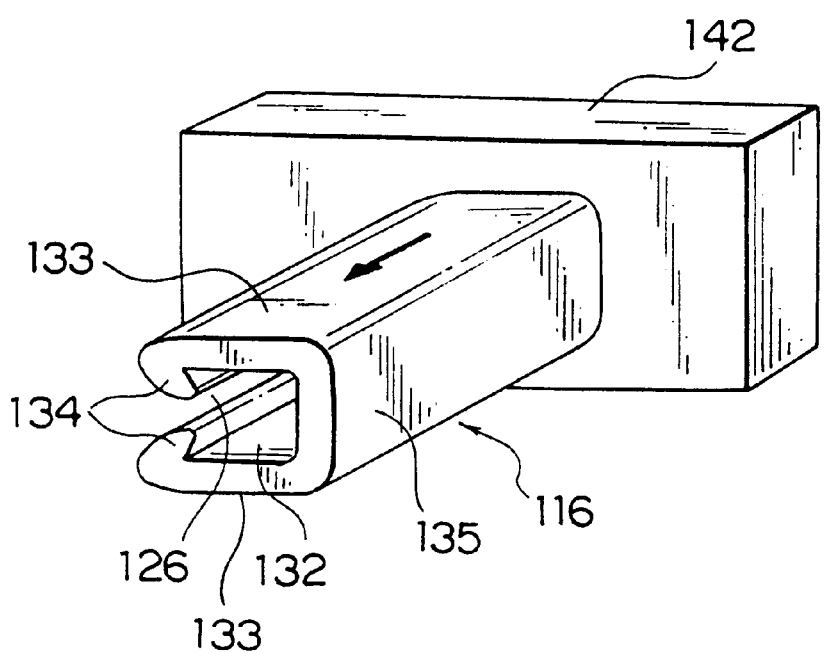
FIG. 32 is a perspective view showing a manufacturing method of the female member of the engaging member according to this embodiment.
Figure 33:
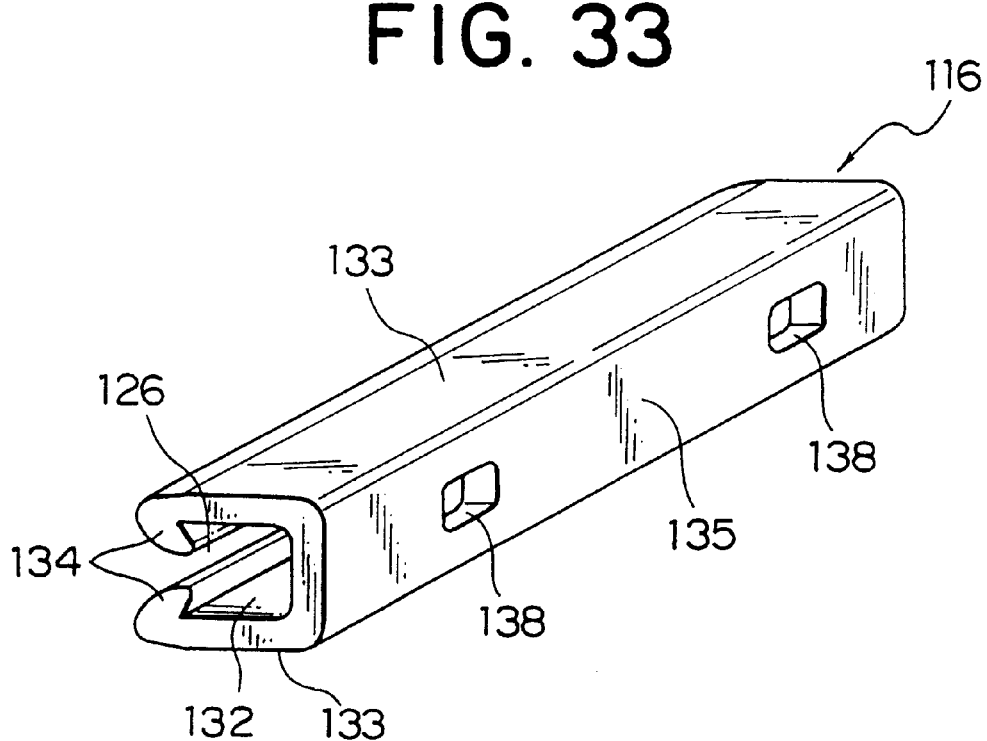
FIG. 33 is a perspective view showing the female member of the engaging member according to this embodiment.

Next, a manufacturing method of the engaging member 112 of this embodiment will be described. The male member 114 and the female member 116 are formed continuously as a long member by extrusion from extruding dies 140 and 142 as shown in FIGS. 30 and 32. Next, this male member 114 as a long member, is punched to the shape of the wave-like engaging pieces 124 as shown in FIG. 31 by means of a die (not shown) or the like so that a portion indicated by two dot/dash line on a side edge is removed out. Alternatively, this portion may be removed to leave the shape of waves by laser beam or the like. The side wall portion 135 of the accommodating portion 132 of the female member 116 is punched out at a predetermined pitch so as to form the through holes 138 as shown in FIG. 33. The punching operation is carried out several times repeatedly while shifting the long male member 114 and female member 116 at a predetermined pitch. After that, the male member 114 and female member 116 are cut out into a predetermined length depending on the application. A lower end of the female member 116 in the insertion direction of the male member 114 is fused by heat so as to form a fused portion 144 thereby preventing the male member 114 from being slipped out. A position of the fused portion 144 is set up such that the engaging pieces 124 engage with the through holes 138 when the male member 114 is inserted up to the fused portion 144 of the female member 116.

Figure 27:
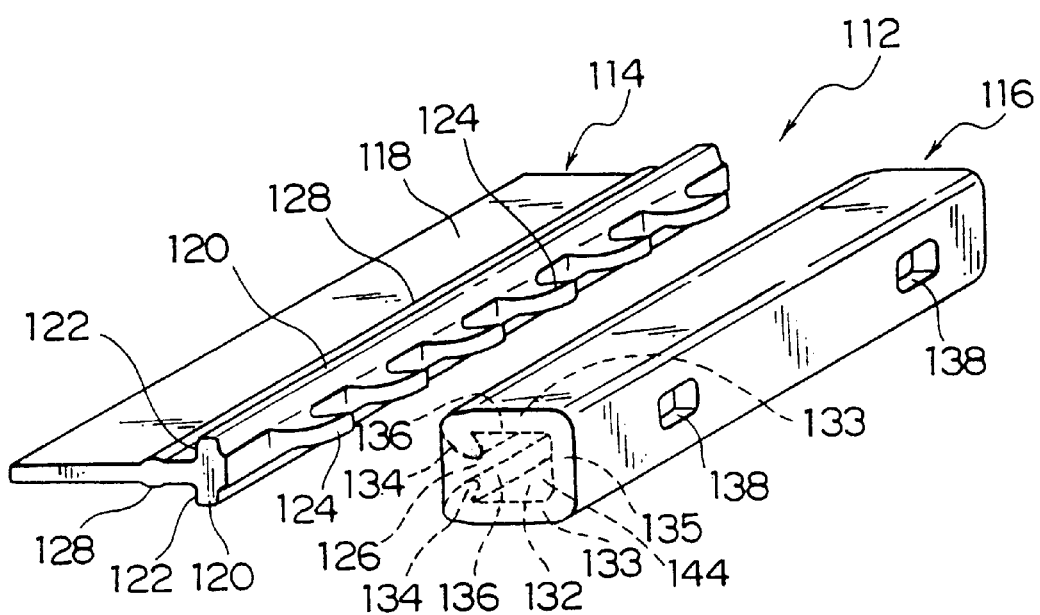
FIG. 27 is a perspective view of the male member and female member of the engaging member according to a fifth embodiment of the present invention.
Figure 28:
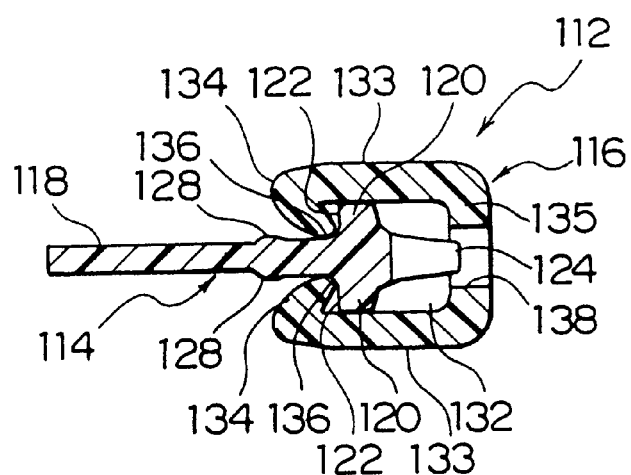
FIG. 28 is a sectional view along a plane perpendicular to the longitudinal direction of the engaging member according to this embodiment.
Figure 29:
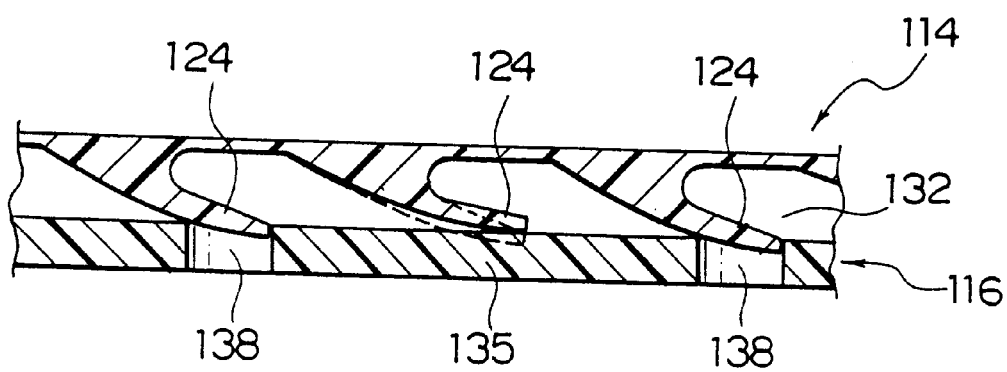
FIG. 29 is a sectional view along a plane parallel to the longitudinal direction of the engaging member according to this embodiment.

Next, the method of use of the engaging member 112 of this embodiment will be described. When it is intended to engage the male member 114 with the female member 116, an end left downward of the male member 114 in FIG. 27 is inserted through an end right upward of the female member 116 in FIG. 27, with the engaging projecting portion 120 of the male member 114 being inserted into the accommodating portion 132 of the female member 116. At this time, the base portion 118 of the male member 114 is located within the opening 126 of the female member 116. Upon the insertion, the respective engaging pieces 124 of the male member 114 are fitted to the through holes 138 of the female member 116. If the male member 114 is pressed into the female member 116 with a stronger force than a predetermined level, as shown in FIG. 29, the respective engaging pieces 124 are elastically distorted so that the engaging pieces 124 ride over and are inserted into the through holes 138. Further, because an outside face of the engaging piece 124 of the male member 114 is inclined with respect to the insertion direction of the male member 114, if some extent of force is applied when the male member 114 is inserted, the engaging pieces 124 can go over the through holes 138 easily. Consequently, the male member 114 can slide easily in the accommodating portion 132 of the female member 116. Then, a lower end of the male member 114 comes into contact with the fused portion 144 at a lower end of the female member 116 and is stopped.

With this state, as shown in FIG. 29, ends of some of the engaging pieces 124 of the male member 114 engage with inner faces of the through holes 138 in the female member 116 thereby preventing the male member 114 from being slipped out in a direction opposite to the insertion direction. Further because ends of the other engaging pieces 124 not engaging with the through holes 138 press elastically an inner face of the side wall portion 135 of the accommodating portion 132, the engaging faces 122 of the engaging projecting portion 120 of the male member 114 make firm contact with the engaged faces 136 of the hook-shaped portions 134 of the female member 116 so that the engagement between the male member 114 and the female member 116 never becomes loose. Further, when a force is applied in such a direction perpendicular to the longitudinal direction that the male member 114 and the female member 116 depart from each other, the engaging faces 122 of the engaging projecting portion 120 of the male member 114 come into contact with the engaged faces 136 of the hook-shaped portion 134 of the female member 116 thereby preventing the male member 114 from being slipped out of the opening 126 of the female member 116.

Figure 34:
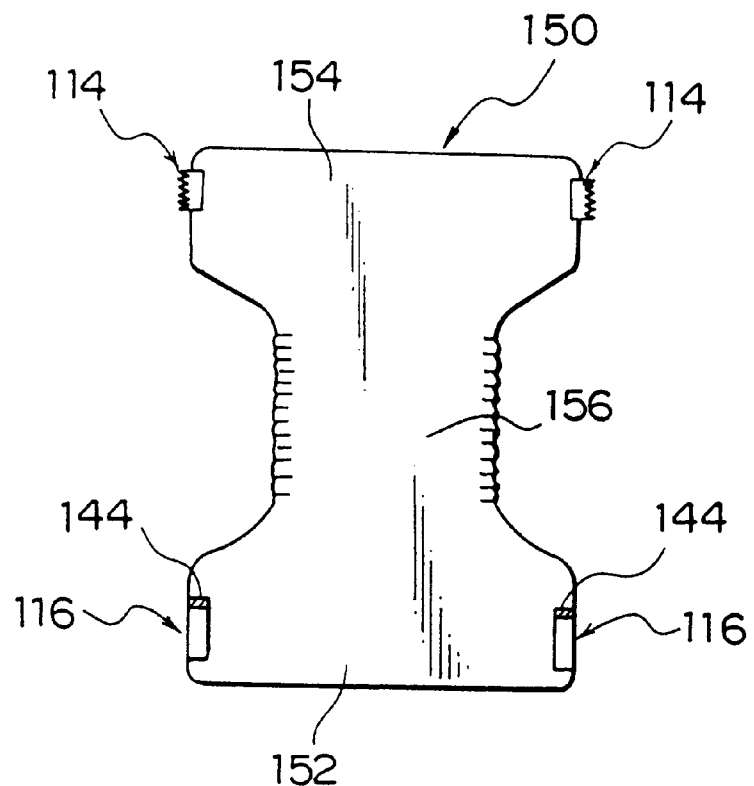
FIG. 34 is a plan view showing an example of use of the engaging member according to this embodiment.

As an example of use, the engaging member 112 of this embodiment can be applied to a disposable diaper 150 as shown in FIG. 34. The disposable diaper 150 is comprised of a buttock portion 152 for wrapping the buttocks, an abdomen portion 154 for wrapping the abdomen and a narrow crotch portion 156 located between the buttock portion 152 and the abdomen portion 154. The female members 116 of the engaging members 112 are attached to both side portions of the buttock portion 152 such that one of the front and rear wall portions 133 of each female member 116 is in contact with each side portion thereof by using adhesive agent, fusion or the like. Then, the male members 114 of the engaging members 112 are attached to both side portions of the abdomen portion 154 such that one side face of the base portion 118 of each thereof is in contact with each side portion by using adhesive agent, fusion or the like. Meanwhile it is permissible to provide integrally or separately the disposable diaper 150 with a reinforcement piece, which is in contact with the side wall portion 135 or the other front and rear wall portion 133 in case of the female member 116 and other side face of the base portion 118 in case of the male member 114, in order to increase attachment strength of the male member 114 and the female member 116. Then, by putting the disposable diaper 150 on the body of a wearer such as a baby or a person who needs to be taken care of, both side portions of the buttock portion 152 and abdomen portion 154 are matched with each other near both sides of the abdomen and the female member 116 is inserted into the male member 114 and engaged therewith.

According to the engaging member 112 of this embodiment, by sliding the male member 114 along the longitudinal direction of the female member 116, they can be connected with each other easily. Even if a force is applied to the male member 114 or female member 116 in a direction that the male member 114 is pulled out or in a direction perpendicular to the longitudinal direction of the female member 116 that the male member 114 departs from the female member 116, the engagement is never released so as to ensure the safety. Particularly when the engaging member 12 is used in the disposable diaper 150 or the like made of soft material, the pressing operation or the like is difficult to carry out because the material has no stiffness. However, according to the engaging member 112 of this embodiment, the male and female members only have to be slid relative to each other along the longitudinal direction so as to achieve the engagement, thereby the pressing operation or the like is not necessary. Thus, the inserting operation in the longitudinal direction can be carried out easily. Further, when this engaging member 112 is applied to the disposable diaper 150, there is no possibility that the wearer's abdomen may be pushed upon engagement of the engaging member 112, so that no discomfort is given to him or her. Further, because the engagement is carried out by insertion, the opening 126 in the main body 128 of the female member 116 does not have to be opened widely upon the engagement, and therefore, this engaging member can be made of hard material. Therefore, this engaging member can be provided with a strong connecting force. Further, because the engaging pieces 124 are elastically deformed and when accommodated in the female member 116, the deformation of the engaging pieces 124 is released in the through holes 138 so that the engaging pieces 124 engage with the through holes 138. Therefore, upon the insertion, no large force is needed, thereby facilitating the insertion operation.

Figure 35:
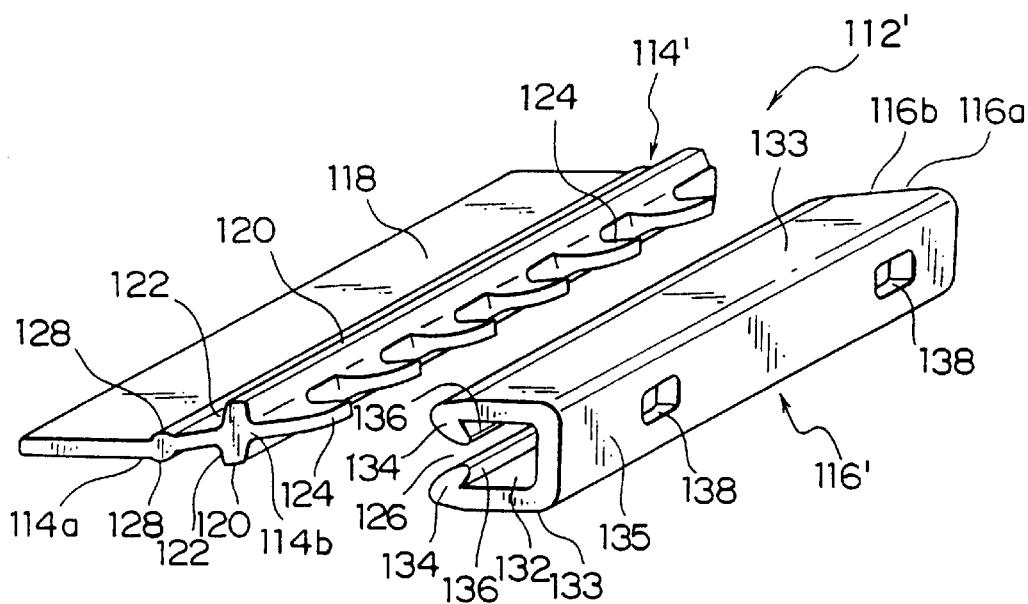
FIG. 35 is a perspective view showing the male member and female member of the engaging member according to a sixth embodiment of the present invention.

Next, a sixth embodiment of the present invention will be described with reference to FIG. 35. The same reference numerals are attached to the same components as the above described fifth embodiment and a description thereof is omitted. The engaging member of this embodiment is comprised of a male member 114' and a female member 116'. A corner on the side of the engaging piece 124 of a front end portion 114a in the insertion direction of the male member 114' is cut out obliquely so as to form an inclined face 114b. Further, an end portion 116a of the female member 116' in which the male member 114' is to be inserted is also cut out obliquely toward the side of the opening 126 with respect to the insertion direction of the male member 114' so as to form an inclined insertion opening 116b.

In the engaging member 112' of this embodiment, the inclined face 114b is formed on the end portion 114a in the insertion direction of the male member 114' so that the end portion 114a is so shaped to facilitate the insertion. Further, the insertion end portion 116a of the female member 116' is also cut out obliquely so as to form the inclined insertion opening 116b thereby ensuring a wide opening area. Consequently, inserting of the male member 114' into the female member 116' is facilitated. Meanwhile, this oblique cut portion may be formed on either the male member 114' or the female member 116'.

Figure 36:
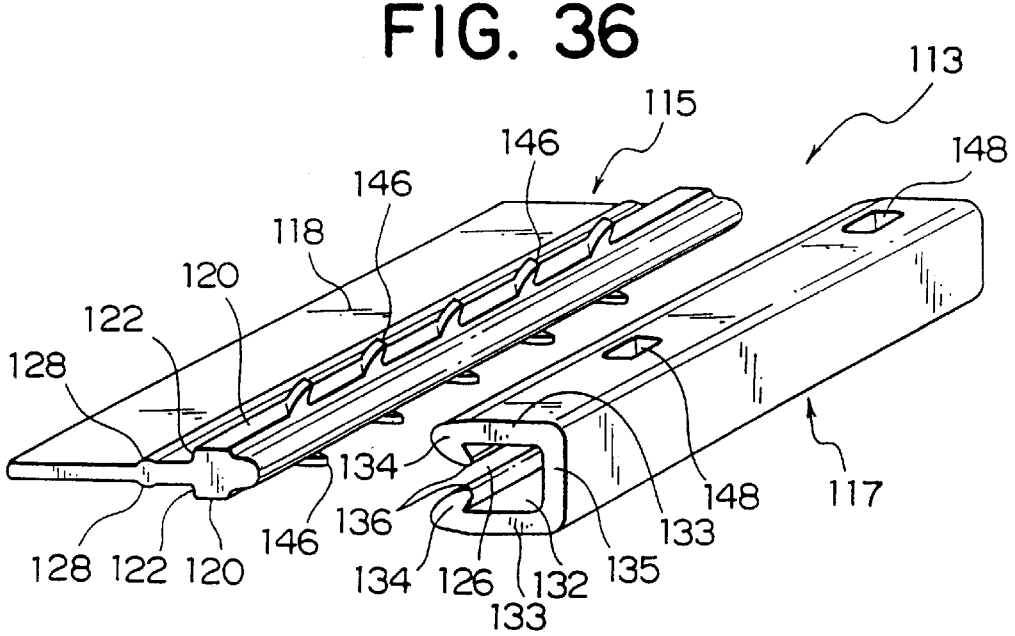
FIG. 36 is a perspective view of the male member and female member of the engaging member according to a seventh embodiment of the present invention.
Figure 37:
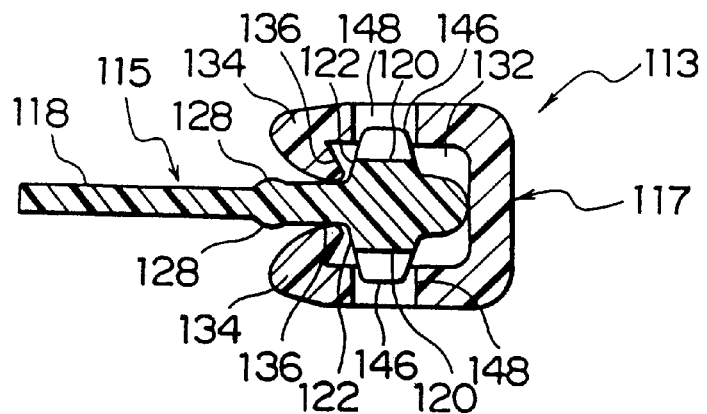
FIG. 37 is a sectional view along a plane perpendicular to the longitudinal direction of the engaging member according to this embodiment.
Figure 38:
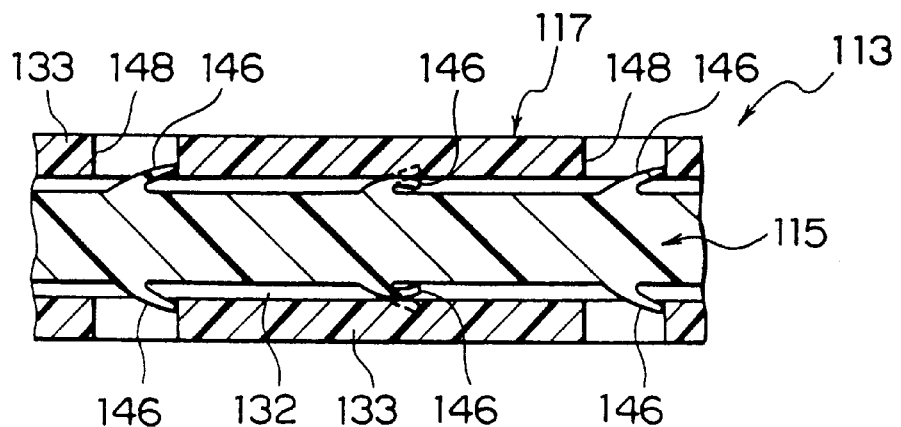
FIG. 38 is a sectional view along a plane parallel to the longitudinal direction of the engaging member according to this embodiment.

Next, a seventh embodiment of the present invention will be described with reference to FIGS. 36 to 38. For an engaging member 113 of this embodiment, the same reference numerals are attached to the same components as the above described fifth embodiment and a description thereof is omitted. According to this embodiment, a plurality of wave-like engaging pieces 146 are formed at a predetermined pitch on the sides of each engaging projecting portion 120 formed in the longitudinal direction of the male member 114. The engaging pieces 146 are capable of being elastically deformed in a direction opposite to the insertion direction and has the same function as the engaging pieces 124 of the fifth embodiment. Through holes 148, which are engaged portions with which the engaging pieces 146 of the male member 115 engage, are formed at a predetermined pitch in the front and rear wall portion 133 of a female member 117.

The engaging member 113 of this embodiment is formed by extrusion and post processing like the above described fifth embodiment.

According to the engaging member 113 of this embodiment, in addition to the same effect as the above fifth embodiment, the engaging force is so strong that the engagement between the male member 115 and the female member 117 is not likely to be released because the engaging pieces 146 are formed on both sides along the engaging projecting portion 120.

Figure 39:
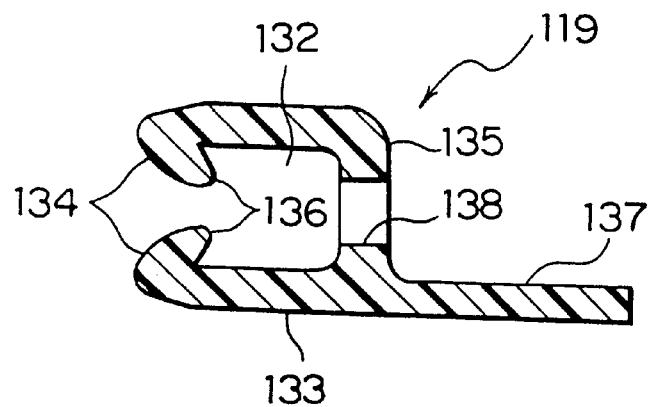
FIG. 39 is a sectional view showing the female engaging member of the engaging member according to an eighth embodiment according to this embodiment.

Next, an eighth embodiment of the present invention will be described with reference to FIG. 39. For the engaging members of this embodiment, the same reference numerals are attached to the same components as the above fifth embodiment and a description thereof is omitted. According to this embodiment, a flat attaching piece 137 is provided on an outside face of the side wall portion 135 of a female member 119 such that it extends in an opposite direction to the front and rear wall portion 133 and parallel to the longitudinal direction of the female member 119. As a result, if the female member 119 is attached to the disposable diaper or the like, the contact area increases so that the female member can be bonded or fused firmly.

Figure 40:
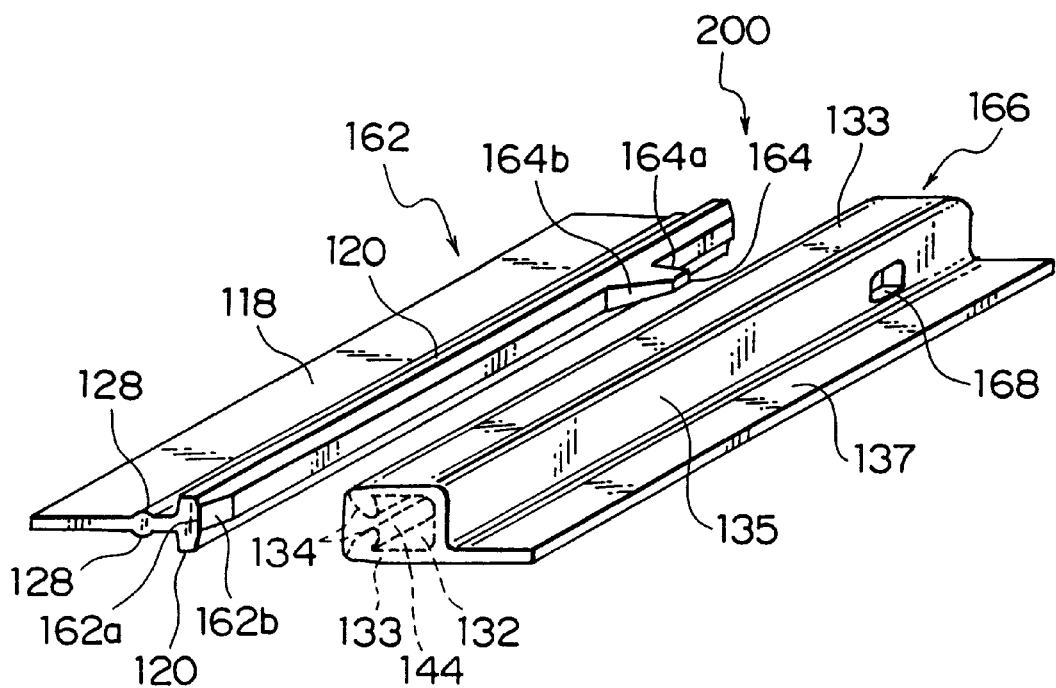
FIG. 40 is a perspective view of the male member and female member of the engaging member according to a ninth embodiment of the present invention.
Figure 41:
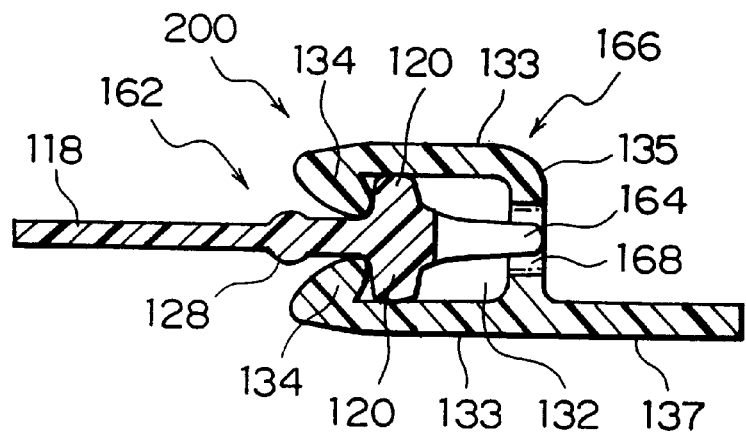
FIG. 41 is a sectional view along a plane perpendicular to the longitudinal direction of the engaging member according to this embodiment.
Figure 42:
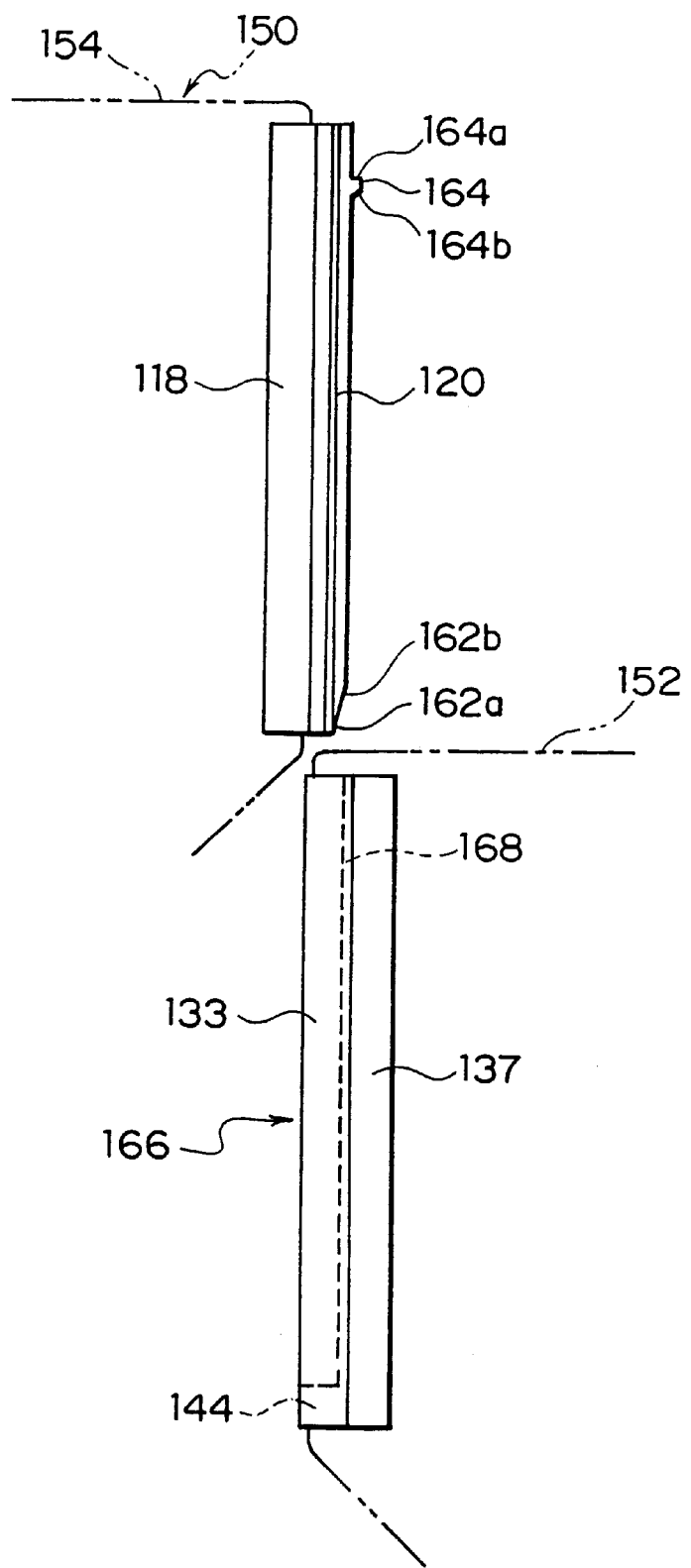
FIG. 42 is a plan view showing an example of use of the engaging member according to this embodiment.

Next, a ninth embodiment of the present invention will be described with reference to FIGS. 40 to 42. For an engaging member 200 of this embodiment, the same reference numerals are attached to the same components as the above fifth to seventh embodiments and a description thereof is omitted. According to this embodiment, one substantially trapezoidal engaging piece 164 is formed in the longitudinal direction on a longitudinal edge of the male member 162. Unlike the engaging piece 124 of the fifth embodiment, the engaging piece 164 is unlikely to be elastically flexed or deformed. The female member 166 has a through hole 168 which is an engaged portion with which the engaging piece 164 of the male member 162 engages, provided at a position of the side wall portion 135. The engaging piece 164 and through hole 168 are formed on the side of the proximal end with respect to the insertion direction of the male member 162.

The female member 166 of this embodiment is formed of a material more flexible than the male member 162. When the male member 162 engages with the female member 166, with the engaging piece 164 inserted into the accommodating portion 132, the female member 166 is elastically deformed so as to allow an insertion of the engaging piece 164. When the engaging piece 164 is located at the through hole 168, the female member 166 is restored from the elastic deformation so that the engaging piece 164 engages with the through hole 168. The engaging piece 164 has a face 164a at right angle with respect to the longitudinal direction of the male member 162 from the front end to the proximal end and a face 164b inclined downward with respect to the longitudinal direction of the male member 162. Therefore, like the above described embodiment, the male member 162 can be inserted easily and the engaging piece 164 engages with the through hole 168 securely.

The engaging member 200 of this embodiment is manufactured by extrusion and post processing like the fifth embodiment. The fused portion 144 is formed by fusing the female member 166 by heat at its bottom in the insertion direction of the male member 162, thereby preventing the male member 162 from being slipped out. The position of the fused portion 144 is set up so that the engaging piece 164 engages with the through hole 138 when the male member 162 is inserted up to the fused portion 144 of the female member 166.

If the male member 162 and female member 166 are formed of the same material, the female member is formed to be harder due to a difference of the sectional shape, that is, sectional coefficient. However, because the female member 166 of the engaging member 200 of this embodiment is formed of more flexible material than the male member 162, the flexibility of the male member 162 and the female member 166 can be adjusted to the same level. Particularly when this engaging member 200 is applied to the disposable diaper 150, feeling of wearing this diaper is excellent because the female member 166 is flexible. Further, because the engaging piece 164 of the male member 162 is hardly elastically deformed, the engaging force of the engaging piece is so strong that it never gets out of the engagement accidentally.

Like the sixth embodiment, the corner at a front end portion 162a in the insertion direction of the male member 162 is cut out obliquely so as to form an inclined face 162b. Thus, the male member 162 can be inserted into the female member 166 easily. Meanwhile, this oblique cut portion may be formed at either or both of the male member 162 and the female member 166.

Figure 43:
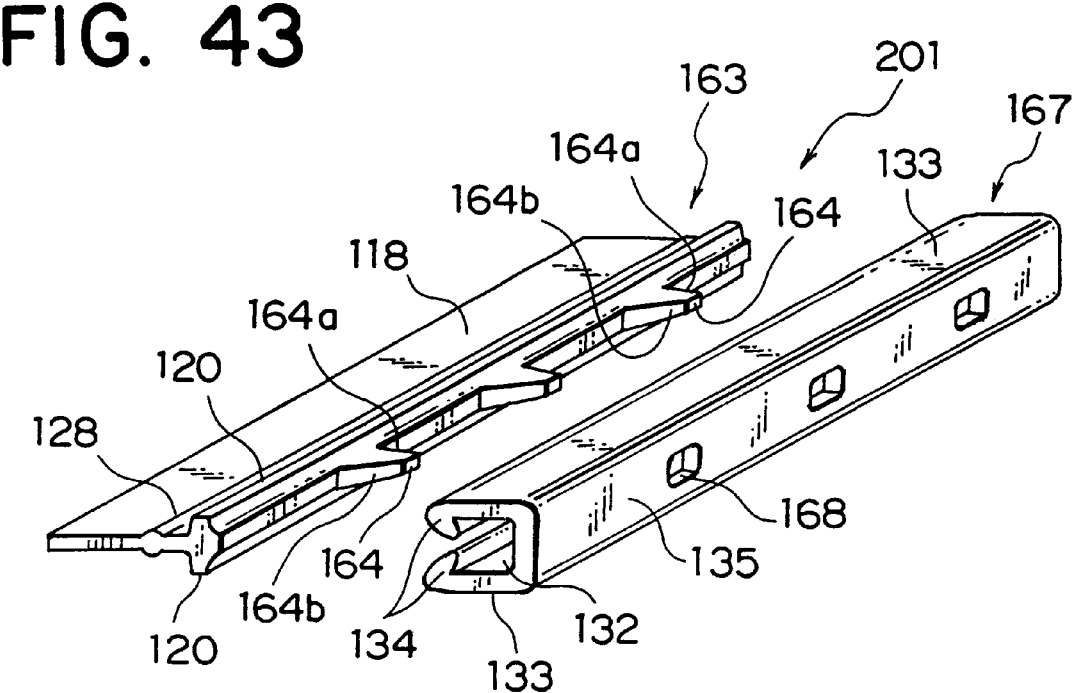
FIG. 43 is a perspective view of the male member and female member of the engaging member according to a tenth embodiment of the present invention.
Figure 44:
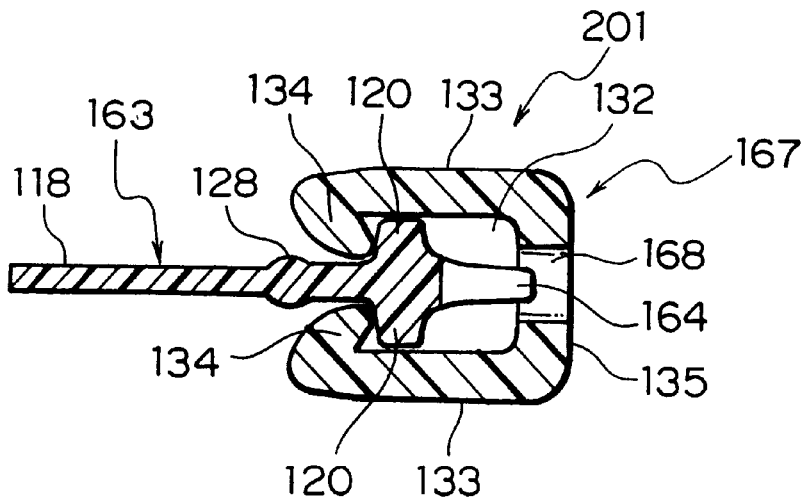
FIG. 44 is a sectional view along a plane perpendicular to the longitudinal direction of the engaging member according to this embodiment.

Next, a tenth embodiment of the present invention will be described with reference to FIGS. 43 and 44. For an engaging member 201 of this embodiment, the same reference numerals are attached to the same components as the above ninth embodiment and a description thereof is omitted. According to this embodiment, a plurality of the substantially trapezoidal engaging pieces 164 are formed in the longitudinal direction on a longitudinal edge of a male member 163. Unlike the engaging piece 124 of the fifth embodiment, the engaging pieces 164 are hardly elastically distorted. Further, a plurality of the through holes 168 which are engaged portions with which the engaging pieces 164 of the male member 163 engage are formed at predetermined positions of the side wall portion 135 of the female member 167. The engaging pieces 164 and through holes 168 are formed at an equal pitch so that they engage with each other when inserted.

The female member 167 of this embodiment is also formed of more flexible material than the male member 163. When it is intended to engage the male member 163 with the female member 167, with the engaging piece 164 inserted into the accommodating portion 132, the female member 167 is elastically deformed so as to allow an insertion of the engaging piece 164. When the engaging piece 164 is located at the through hole 168, the female member 167 is restored from the elastic deformation, so that the engaging pieces 164 engages with the through holes 168 securely. The engaging member 201 of this embodiment is also formed by extrusion and post processing like the above fifth embodiment.

According to this embodiment, in addition to the same effect as the ninth embodiment, a securer engagement is realized.

Figure 45:
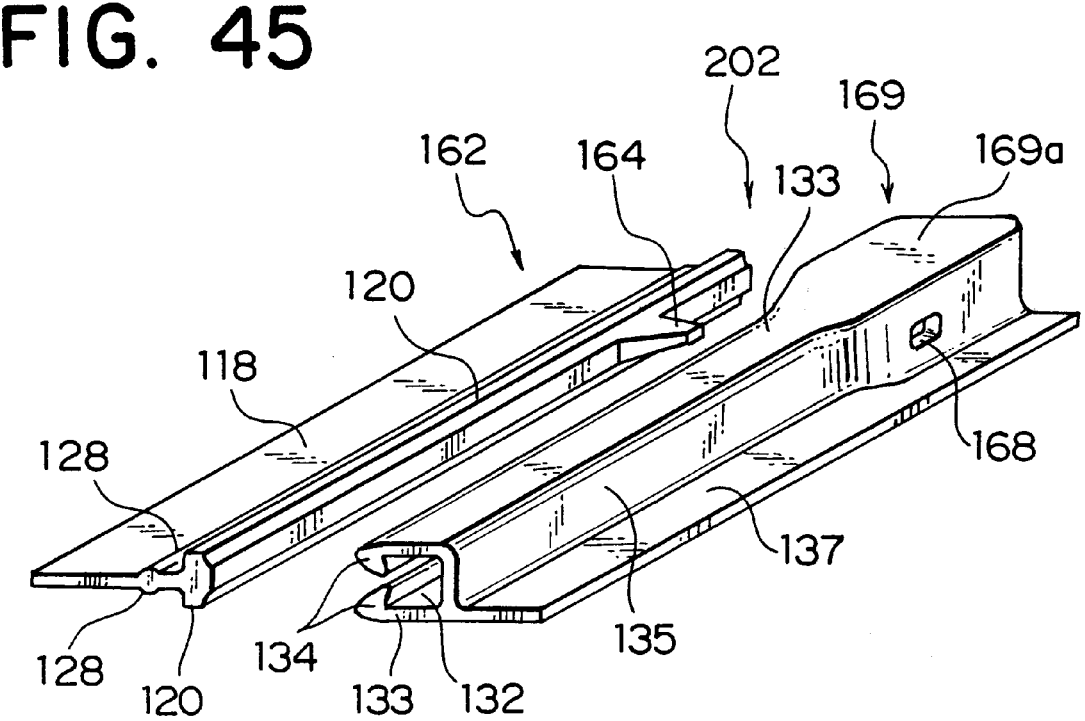
FIG. 45 is a perspective view of the male member and female member of the engaging member according to an eleventh embodiment of the present invention.
Figure 46:
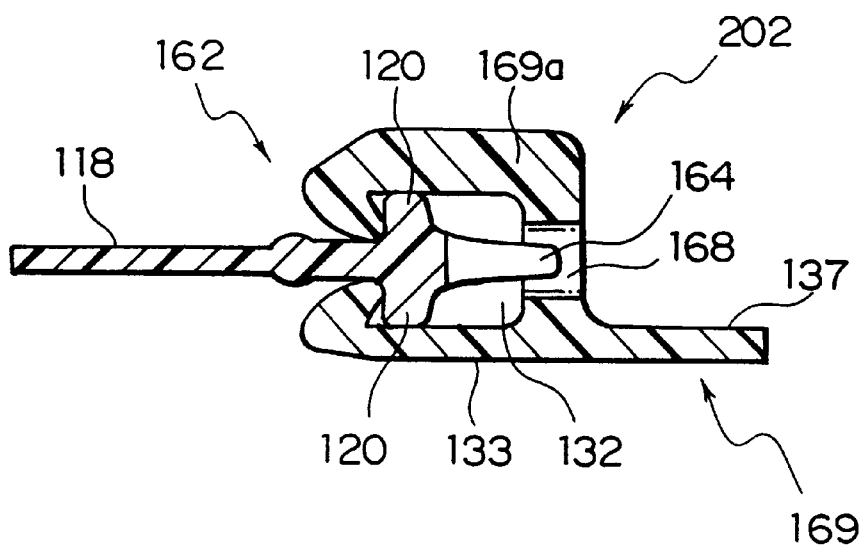
FIG. 46 is a sectional view along a plane perpendicular to the longitudinal direction of the engaging member according to this embodiment.

An eleventh embodiment of the present invention will be described with reference to FIGS. 45 and 46. For an engaging member 202 of this embodiment, the same reference numerals are attached to the same components as the above described ninth embodiment and a description thereof is omitted. The male member 162 of this embodiment is the same member as used in the ninth embodiment. A female member 169 contains a thick end portion 169a in the longitudinal direction thereof, in which the through holes 168 which are engaged portions and the engaging piece 164 of the male member 162 engages with are formed.

The engaging member 202 of this embodiment is formed by extrusion and post processing like the above described fifth embodiment. This thick end portion 169a may be formed by pasting resin which is the same as other portions to this portion or integral molding the thick end portion 169a with a molding die.

The female member 169 of this embodiment is also formed of more flexible material than the male member 162. When the male member 162 engages with the female member 169, with the engaging piece 164 inserted into the accommodating portion 132, the female member 169 is elastically deformed so as to allow the engaging piece 164 to be inserted. Then, when the engaging piece 164 is located at the through hole 168, the female member 169 is restored from its elastic deformation so that the engaging piece 164 engages with the through hole 168 securely.

According to this embodiment, in addition to the same effect as the above described ninth embodiment, a securer engagement is realized.

Meanwhile, the engaging member of the present invention is not restricted to the above described respective embodiments, but the quantity and shape of the engaging portion and engaging piece can be changed freely. In the engaging member of the present invention, the engaging portion or engaging piece may be releasable or may not be releasable from the engaged portion. For example, the engagement may be released by pressing the engaging piece in the engaged portion or it is permissible to provide with a member for releasing the engagement of the engaging piece. When this engaging member is used in a disposable diaper formed of unwoven cloth, when the diaper is removed from a body, it is permissible to break the unwoven cloth so as to remove the diaper and the engaging member does not always have to be attached or detached freely. Further, the engaging portion and engaged portion may be formed in the same shape and any shape, for example, triangular wave, rectangular wave, trapezoidal wave or the like may be applied as long as it is capable of engaging. Further, this engaging member can be used in various connecting members, fastening members and the like as well as the disposable diaper. The male member and the female member may be attached to the disposable diaper or the like by other attachment method than bonding and fusion, the male member and the female member may be provided with an attachment piece for bonding or fusion. This engaging member can be used in various connecting members, fastening members and the like as well as the disposable diaper.

The engaging member of the invention has a strong engaging force and would not get disengaged even if a force in various directions is applied to it, so that it is safe. The engaging operation can be carried out easily, in which the male member is slid into the female member from an end portion thereof longitudinally, so that a force is not applied to the male member and the female member to deform them, and they can be disengaged easily. With at least one of the insertion end portions of the male member and female member is cut off obliquely, the insertion operation is further facilitated.

In the male member and female member of the invention, it is possible to make the rigidity of both members identical, so that the engaging member can be relatively flexible and comfortable to wear in case of application for a person.

Further, the manufacturing method of the engaging member of the invention, the engaging member with a strong engaging force can be formed easily which realizes low cost and stable quality.

What is claimed is:

1. An engaging member comprising components to be connected with each other, a male member to be attached on one of the components and a female member to be attached on the other of the components, engaging projecting portions with which the female member engages being provided on a side edge in a longitudinal direction of said male member, said female member comprising an accommodating portion formed along a longitudinal direction so as to accommodate said male member and hook-shaped portions with which the engaging projecting portion of said male member engages being formed along the longitudinal direction inside the accommodating portion, the longitudinal direction substantially perpendicular to an upper face of the engaging projecting portions of the male member, wherein said male member has an engaging portion, which comprises a face inclined downward with respect to the longitudinal direction of said male member from a front end to a proximal end and said accommodating portion of said female member comprises an engaged portion, which allows a sliding of said male member and female member in one longitudinal direction thereof and said engaging portion is engaged with in an opposite direction with respect to the longitudinal direction.

2. An engaging member according to claim 1, wherein a plurality of said engaging portion are formed continuously along the engaging projecting portion of said male member and a plurality of said engaged portions are formed in the accommodating portion of said female member along the longitudinal direction.

3. An engaging member according to claim 1, wherein said engaging portion has a face at a right angle with respect to the longitudinal direction of said male member and the face inclined downward with respect to the longitudinal direction of said male member from the front end to the proximal end.

4. An engaging member according to claim 1, wherein the engaging projecting portion of said male member is inserted from an end portion in the longitudinal direction of the accommodating portion of said female member by sliding in parallel relative to each other so that the male member engages with the female member.

5. An engaging member comprising components to be connected with each other, a male member to be attached on one of the components and a female member to be attached on the other of the components, an engaging projecting portion with which said female member engages being provided on a side edge in a longitudinal direction of said male member, said female member comprising an accommodating portion formed along a longitudinal direction so as to accommodate said male member, and hook-shaped portions with which the engaging projecting portion of said male member engages being formed along the longitudinal direction inside the accommodating portion, the longitudinal direction substantially perpendicular to an upper face of the engaging projecting portion of the male member, wherein said male member has engaging pieces formed to extend at a predetermined pitch and elastically deformed within the accommodating portion of said female member and said female member contains at least an engaged portion provided in the accommodating portion, which allows a sliding of said male member and female member in one longitudinal direction thereof and the engaging pieces are engaged with in an opposite direction with respect to the longitudinal direction.

6. An engaging member according to claim 5, wherein said engaging pieces are extended inclinedly in an opposite direction with respect to the insertion direction into the female member and said engaged portion is composed of a concave portion formed within said accommodating portion.

7. An engaging member according to claim 5, wherein the engaging projecting portion of said male member is provided to protrude on both side faces along the longitudinal direction of the male member while said engaging pieces are formed continuously along a side edge in the longitudinal direction of said male member.

8. An engaging member according to claim 5, wherein at least one of end portions opposing each other when the male member and the female member engage with each other is cut out obliquely with respect to the insertion direction.

9. An engaging member comprising components to be connected with each other, a male member to be attached on one of the components and a female member to be attached on the other of the components and formed to be more flexible than said male member, engaging projecting portions with which the female member engages being provided on a side edge in a longitudinal direction of said male member, said female member comprising an accommodating portion formed so as to accommodate said male member and hook-shaped portions with which the engaging projecting portion of the male member engages being formed along a longitudinal direction inside the accommodating portion, the longitudinal direction substantially perpendicular to an upper face of the engaging projecting portions of the male member, wherein said male member has one or a plurality of engaging pieces formed so as to extend sideways thereof such that said male member is capable of sliding within the accommodating portion of the female member while deforming the female member and said female member contains one or a plurality of engaged portions which allow a sliding of said male member and female member in one longitudinal direction thereof and said engaging pieces are engaged with in an opposite direction with respect to the longitudinal direction.

\* \* \* \* \*